United States Patent
Trier

(10) Patent No.: US 6,710,051 B1
(45) Date of Patent: Mar. 23, 2004

(54) SCREENING METHOD

(75) Inventor: Klaus Trier, Hellerup (DK)

(73) Assignee: Klaus Trier APS, Hellerup (DK)

( * ) Notice: Subject to any disclaimer, the term of this patent is extended or adjusted under 35 U.S.C. 154(b) by 0 days.

(21) Appl. No.: 09/341,169

(22) PCT Filed: Jan. 5, 1998

(86) PCT No.: PCT/DK98/00001

§ 371 (c)(1),
(2), (4) Date: Jul. 6, 1999

(87) PCT Pub. No.: WO98/30900

PCT Pub. Date: Jul. 16, 1998

(30) Foreign Application Priority Data

| Jan. 6, 1997 | (DK) | 0009/97 |
| Jul. 7, 1997 | (DK) | 0823/97 |
| Dec. 1, 1997 | (DK) | 1383/97 |

(51) Int. Cl.$^7$ .................. A01N 43/90; A61K 31/52
(52) U.S. Cl. .................. 514/262.1; 514/263.1; 514/263.2
(58) Field of Search .................. 514/336, 330, 514/262.1, 263.1, 263.2

(56) References Cited

U.S. PATENT DOCUMENTS

| 4,425,346 A | * | 1/1984 | Horlington | 424/253 |
| 4,942,161 A | | 7/1990 | Tiburtius | |
| 5,055,302 A | | 10/1991 | Laties et al. | |
| 5,086,061 A | | 2/1992 | Tiburtius | |
| 5,122,522 A | | 6/1992 | Laties et al. | |
| 5,521,168 A | | 5/1996 | Clark | |
| 5,626,865 A | * | 5/1997 | Harris et al. | 424/427 |

FOREIGN PATENT DOCUMENTS

| DE | 4207366 | | 4/1993 |
| EP | 0556947 | | 8/1993 |
| WO | 9015604 | * | 12/1990 |
| WO | 9313777 | * | 7/1993 |
| WO | 8423719 | | 10/1994 |
| WO | 9425034 | | 11/1994 |

OTHER PUBLICATIONS

Ashihara, H., et al., "Catabolism of Caffine and Related Purine Alkaloids in Leaves of Coffee Arabica L.," *Planta* 198:334–339 (1996).

Bjornsson, S., et al., "Simultaneous Preparation and Quantiation of Proteoglycans by Precipitation with Alcian Blue," *Analytical Biochemistry* 210:282–291 (1993).

Blach, R.K., et al., "Electrical Activity of the Eye in High Myopia," *Brit. J. Ophthal.* 50:629–641 (1966).

Bragadottir, R., et al., "Serotonin Elevates the c–wave of the Electroretinogram of the Rabbit Eye by Increasing the Transepithelial Potential," *Vision Res.* 37–18:2495–2503 (1997).

Abstract of "Eyedrops for Curing Myopia," CN1108539 A 950920).

Cottriall, C.L., et al., "The $M_1$ Muscarinic Antagonist Pirenzepine Reduces Myopia and Eye Enlargement in the Tree Shrew," *Investigative Ophthalmology & Visual Science* 37–7:1368–1379 (1996).

Cox, S.N., et al., "The Effect of Acetazolamide on Electro–oculogram Potential," ARVO Abstracts *Invest Ophthalmol Vis Sci* 29:146.

Creighton, M.O., et al., "Effect of Cyclic Amp, Caffine and Theophylline on Differentiation of Lens Eipthelial Cells," *Nature* 249:767–768 (1974).

Dawis, S.M, et al., "Theophylline Abolishes the Light Peak in Perfused Cat Eyes," *Invest Ophthalmol Vis Sci* 28:700–706 (1987).

Erickson, C.A., et al., "Embryonic Fibroblast Motility and Orientation Can be Influenced by Physiological Electric Fields," *The Journal of Cell Biology* 98:296–307 (1984).

Evangelisti, R., et al., "Coordinate Effects of Concanavalin A on Cytoskeletal Organization, Cell Shape, Glycosaminoglycan Accumulation and Exoglycosidase Activity in Chick Embryonic Cultured Fibroblasts," *Eur. J. Histochem.* 37:161–172 (1993).

Greene, P.R., et al., "Plastic Deformation of Sclera," *Arvo Abstracts* p. 297 (1978).

Hiroi, K., et al., "Effects of Ornithine on the Electroretinogram in Cat Retina," (Abstract) *Invest Ophthalmol & Vis Sci* 36(8):1732–1737 (1995).

Iuvone, P.M., et al., "Effects of Apomorphine, a Dopamine Receptor Agonist, on Ocular Refraction and Axial Elongation in a Primate Model of Myopia," *Invest Ophthalmol Vis Sci* 32(5):1674–1677 (1991).

(List continued on next page.)

Primary Examiner—Alton N. Pryor
(74) Attorney, Agent, or Firm—Iver P. Cooper

(57) ABSTRACT

The invention relates to a method for identification of substances which are applicable for treatment or prevention of an insufficient longitudinal growth of the eye (hypermetropia) or for treatment or prevention of an excessive longitudinal growth of the eye (myopia); substances identified by the method for treating or preventing conditions related to the longitudinal growth of the eye; substances and mixtures of substances for the preparation of a pharmaceutical composition for the treatment or prevention of abnormal growth of the axial length of the eye. The identification involves measuring the effect of the substances on the retinal pigment epithelium of the eye, e.g. by detecting the metabolic effect of the substance on the retinal epithelium, the effect on the standing potential or the effect on the proteoglycanes of the scleral tissue of the eye, by way of EOG examination, by way on the size of the so-called c-wave in ERG-recordings, or by the state of the $Ca^{2+}$-channels or on the [$^3$H]-ryanodine receptors of the retinal pigment epithelium.

28 Claims, 12 Drawing Sheets

OTHER PUBLICATIONS

Jarkman, S., et al., "The DC–ERG as a Highly Sensitive Measure of Effects of Prostaglandins, " *Documenta Ophthalmologica* 60:383–392 (1985).

Jarkman, S., et al., "The C–wave of the Electroretinogram and the Standing Potential of the Eye as Highly Sensitive Measures of Effects of Low Doses of Trichloroethylene, Methylchloroform, and Halothane," *Documenta Ophthalmologica* 60:375–382 (1985).

Jarkman, S., "Influence of Isobutylmethylxanthine on the Direct Current Electroretinogram of Albino Rabbit Eyes," (Abstract) *Documenta Ophthalmologica* 73:163 (1989) p. 163 only.

Jarkman, S., "Effects of Vasoactive Intestinal Peptide (VIP) on the D.C. ERG and on the Standing Potential of Albino Rabbit Eyes," (Abstract) *Clin Vision Sci* 7(2):71 (1992) p. 71 only.

Jarkman, S., "Effects of Low Doses of Forskolin on the C–wave of the Direct Current Electroretinogram and on the Standing Potential of the Eye," *Documenta Ophthalmologica* 67:305–314 (1988).

Jensen, H., "Myopia Progression in Young School Children," *Acta Ophthalmol* Suppl. 200(69) 7–11, 56–59.

Kato, M., et al., "Effects of Quisqualic Acid on the Corneal and Intraretinal Direct–current Electroretinogram and on the Standing Potential of the Rabbit Eye," *Documenta Ophthalmologica* 91:349–362 (1996).

Kawasaki, K., et al., "Acetazolamide–induced Changes of the Membrane Potentials of the Retinal Pigment Epithelial Cell," *Documenta Ophthalmologica* 63:375–381 (1986).

Kirschner, A.J., et al., "The Effects of Caffine on Near Point Plus Acceptance," *J Am Optometric Assoc* 55(2): 97–102 (1984).

Knave B., et al., "The Effect of Barbiturate on Retinal Functions II. Effects on the C–wave of the Electroretinogram and the Standing Potential of the Sheep Eye," (Abstract) *Acta Physiol Scand* 91:180–186 (1974).

Krasnov, M.M., et al., "The Policy of Choosing a Vascular Collector and Method for Drug Administration in Intraarterial Infusion Therapy of the Organ of Vision," *Vestnik Oftalmologii* (1995) ABS only.

Liu, W., et al., "Structure–activity Relationship of Xanthines and Skeletal Muscle Ryanodine Receptor/$Ca^{2+}$ Release Channel," *Pharmacology* 54:135–143 (1997).

McBrien, N.A., et al., "Increased Proteoglycan Synethsis in the Sclera of Tree Shrew Eyes Recovering From Form Deprivation Myopia," *Investigative Ophthalmology & Visual Science* 36(4):760 (1995).

Muller–Limroth, W., "Die Koffein–Wirkung auf das Elektroretinogram des Menschen," *Artzl Forsch* 20(2):86–89 (1966).

Nao–I, N., et al., "Effects of Melatonin on the Chick Retinal Pigment Eipthelium: Membrane Potentials and Light–evoked Responses," (Abstract) *Exp Eye Res* 49:573–589 (1989).

Norton, T.T., et al., "Morphology of Tree Shrew Sclera and Choroid During Normal Development, Induced Myopia, and Recovery," *Invest Ophthalmol Vis Sci* 37(3):324 (1996).

Norton, T.T., et al., "Reduced Extracullular Matrix in Mammalian Sclera with Induced Myopia," *Vision Res* 35(9):1271–1281 (1995).

Saika, S., et al., "Pentoxifylline and Pentifylline Inhibit Proliferation of Human Tenon's Capsul Fibroblasts and Production of Type–I Collagen and Laminin in Vitro," *Ophthalmic Res* 28:165–170 (1996).

Sato, T., et al., "Effect of Dopamine and Haloperidol on the C–wave and Light Peak of Light–induced Retinal Responses in Chick Eye," (Abstract) *Documenta Ophthalmologica* 65:87 (1987) p. 87 only.

Schaeffel, F., et al., "Studies on the Role of the Retinal Dopamine/Melatonin System in Experimental Refractive Errors in Chickens," *Vision Res* 35(9):1247–1264 (1995).

Shpak, et al., "Effectivity of Local Usage of Complamine and Atph in Treatment of Patients with Primary and Secondary Atrophy of the Optic Nerve," *Oftalmologicheskii Zhurnal* 3: (1985) ABS only.

Smelovsky, A.S., et al., "Calcitonin Prophylaxis of Myopia Progress," *Vestnik Oftalmologii* 104(2): (1988).

Szymankiewiczowa, S., "Therapeutic Value of Ionophoresis in Visual System Diseases," (Abstract) Wojewodz. Przych. Okulist, Katoqice, Poland, Klin. Oczna, 47(7) (1997) ABS only.

Textorius, O., et al., "Effects of Intraocular Irrigation with Melatonin on the C–wave of the Direct Current Electroretinogram and on the Standing Potential of the Eye in Albino Rabbits," (Abstract) *Documenta Ophthalmologica* 65:97 (1987) p. 97 only.

Textorius, O., et al., "Effects of Intravitreal Perfusion with Dopamine in Different Concentrations on the DC Electroretinogram and the Standing Potential of the Albino Rabbit Eye," (Abstract) *Documenta Ophthalmologica* 73:149 (1989) p. 149 only.

Trier, K., et al, "Biochemical Changes in Rabbit Sclera Following Destruction of Pigment Epithelium," *Acta Ophthalmologica* 69:645–648 (1991).

Windmeier, C., et al., "Pharmacological Aspects of Pentoxufylline with Emphasis on Its Inhibitory Actions on Hepatic Fibrogenesis," *Gen Pharmac* 29(2):181–196 (1997).

Yonemura, D., et al., "Susceptibility of the Standing Potential of the Eye to Acetazolamide and its Clinical Application," (Abstract) Kinesisk/Japansk Tidsskrift (1978).

Yonemura, D., et al., "Enhancement of the Electroretinographic C–wave with Cysteine," (Abstract) Acta Soc Ophthalmol Jap 81(1) ABS only.

Zhai, H., et al., "The Effect of Caffine on the Accomodative Response/Accomodative Stmulus Function and on the Response AC/A Ration," *Current Eye Research* 12(6):489–499 (1993).

\* cited by examiner

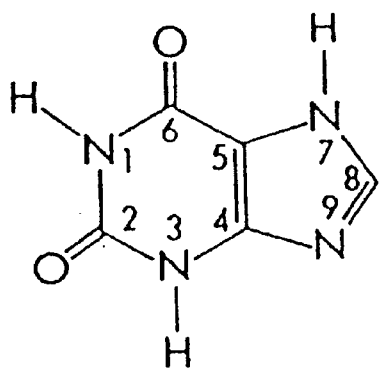
Xanthine
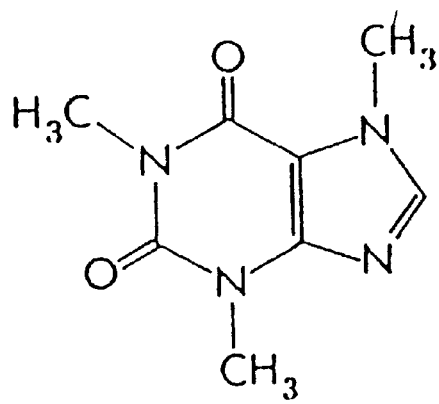
Caffeine
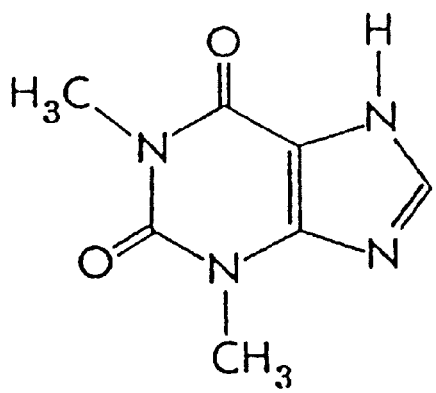
Theophylline
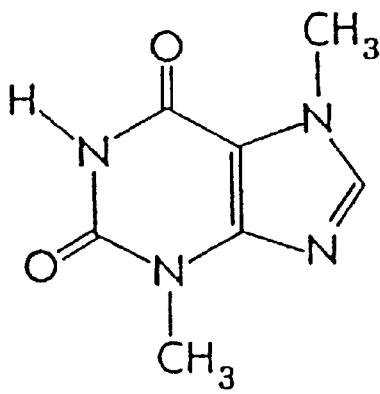
Theobromine
Fig. 3

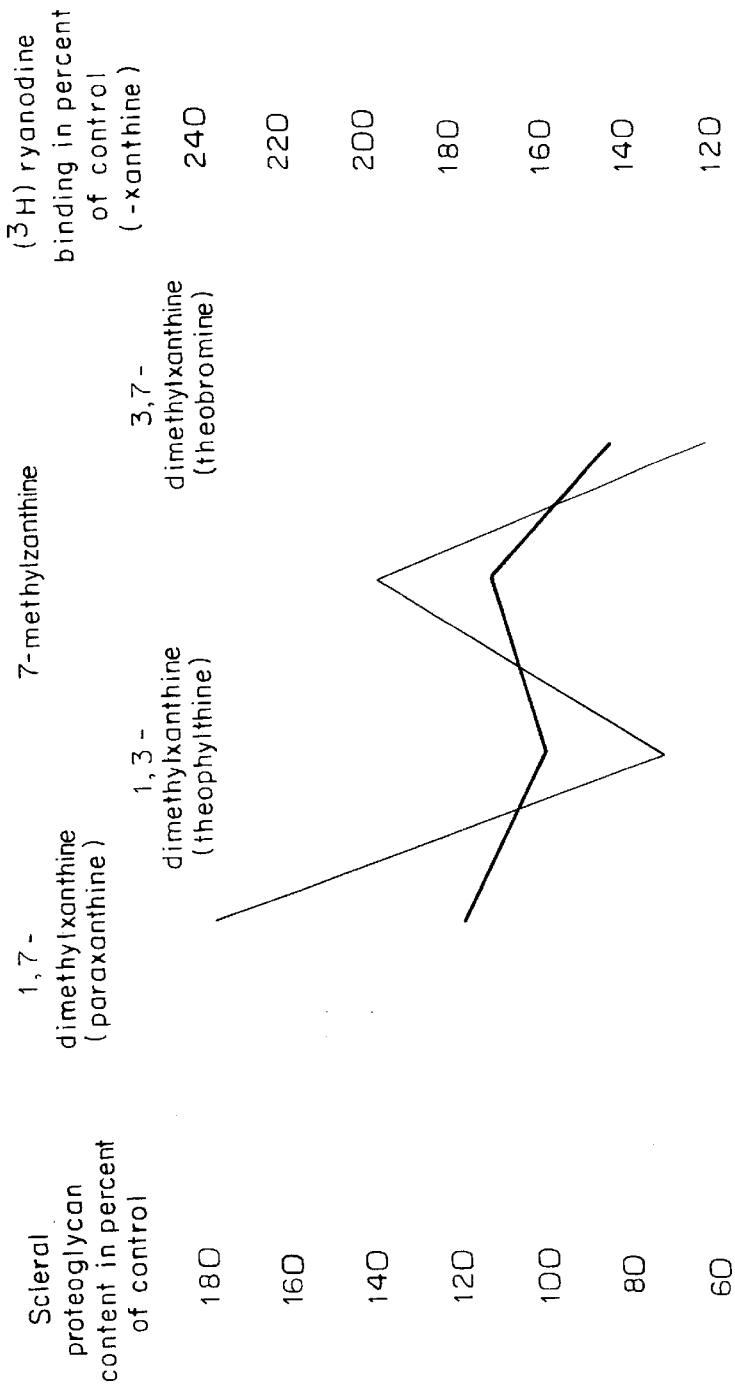

Fig. 12 shows complete correlation between effect of different methylxanthines on content of proteoglycans in posterior sclera (———) and effect on ³H ryanodine binding compared to that of -xanthine (———)

Caffeine is represented by 1,7-dimethylxanthine, since this metabolite dominates in the serum of rabbits after feeding with caffeine. A ³H ryanodine binding exceeding 130% of -xanthine is apparently needed to produce a positive effect on scleral content of proteoglycans.

SCREENING METHOD

CROSS REFERENCE TO RELATED APPLICATION

The present application is the national stage under 35 U.S.C. 371 of PCT/DK98/00001, filed Jan. 5, 1998.

The invention relates to a method for identification of substances which are applicable for treatment or prevention of an insufficient longitudinal growth of the eye (hypermetropia) or for treatment or prevention of an excessive longitudinal growth of the eye (myopia); substances identified by the method for treating or preventing conditions related to the longitudinal growth of the eye; substances and mixtures of substances for the preparation of a pharmaceutical composition for the treatment or prevention of abnormal growth of the axial length of the eye.

BACKGROUND OF THE INVENTION

Myopia is caused by the length of the eye being too big in relation to the optical strength of the cornea and the lens so that the picture of a distant object is focused in a point in front of the retina, whereas the picture produced on the retina will be blurred. In other words, myopia is caused by an anomaly between the length of the eye (the axial length) and the refraction in the cornea and the lens.

The longitudinal growth of the eye (from approximately 17 mm at birth to approximately 24 mm) during the childhood is caused by expansion of the eye content and thus stretching the immature connective tissue in the sclera of the eye which adjusts to the new size of the eye. Normally the eye will reach its permanent length at the age of 12, at which time the connective tissue in the sclera reaches an appropriate degree of maturity and the longitudinal growth of the eye will stop.

In myopic persons the longitudinal growth of the eye is too high and the longitudinal growth of the eye continues for a longer period of time than in normal individuals. Hypermetropia is caused by the length of the eye being too short in relation to the optical strength of the cornea and the lens. Hypermetropia usually prevails at birth and is normally recorded at the age of 3–5 years. Subsequently it will reduce in proportion with the growth of the eye until the age of 12, from which age it will remain constant for the rest of the persons life.

Approximately 25%, of the population are myopic. In some myopic persons the axial length is normal (physiological myopia, of <−4 dioptry), in other persons, the axial length grows from the age of 8–10 unproportionally much until the approximate age of 20, and subsequently the axial length and thus the myopia are stable (intermediary myopia, glass strength of from approximately −4 to −6 dioptries).

Finally, in rare cases a continuously growing axial length throughout the entire life can be seen, often connected with bulges in weak areas of the eye wall (scleraectasies). Here the myopia can reach extreme levels for glass strengths of up to approximately −40 dioptries (Excessive/pathological myopia).

The intermediary form, and the excessive one in particular, is connected to a high risk of severe sight threatening complications such as e.g. retinal detachment, degenerative changes in the yellow spot of the eye (macula degeneration) and glaucoma.

In the Western part of the world, severe myopia is among the most important causes of blindness.

The group of myopic persons with a glass strength of more than −6, which comprises parts of the intermediary group and the entire excessive group, comprises approximately 2% of the population, e.g. in Denmark approximately 100 000 persons (Curtin, B. J.: The myopys: Basic science and clinical management, Harper and Row, Philadelphia, (1985)).

The cause of axial length conditional myopia is unknown.

It is however known that the longitudinal growth of the eye can be increased by disturbance of the image formation on the retina, eg. experimentally by sewing together the eye lids of test animals (visual deprivation) (Yinon, U., Current Eye Research, vol. 3, 4, 677–690, 1984).

Administration of dopaminergic substances (apomorphine) in test animals exposed to visual deprivation inhibits the development of myopia. (Iuvone, P. M., Invest. Ophthalmol., Vis. Sci., 32, 1674–77 (1991)).

U.S. Pat. No. 5,055,302, Laties and Stone, shows a method for control of abnormal postnatal growth of the eye of an animal with the application of vasoactive intestinal peptide (VIP), PH1 or analogues of such peptides. Such peptides were found to restrain the axial longitudinal growth of a myopic eye.

U.S. Pat. No. 5,122,522, Laties and Stone, shows a method for control of abnormal postnatal growth of the eye of an animal with the application of pirenzepine, an anticholinergic substance (M1 Muscarine antagonist). The axial longitudinal growth was inhibited by administration of pirenzepine.

PCT-patent application publication No. WO 94/25034, Laties and Stone, shows a method for control of abnormal postnatal growth of the eye of an animal with the application of tricyclical-substances (antidepressiva). The axial longitudinal growth was inhibited by administration of tricyclical substances.

However, in most cases myopia and hypermetropia are benign conditions which can easily be corrected by means of glasses. In order to justify a medical treatment of these conditions, such treatment must be effective at relatively low dosages and roughly without any side effects, accordingly, as application of VIP, dopaminergic anticholineric or tricyclical substances is connected to risk of side effects as, simultaneously, the substances have considerable psychochemical effects these prior art substances are not suitable for such treatment.

It is also a theory that the growth of the eye can be caused by passive stretching of the scleral connective tissue (Norton, T. T., Invest. Ophthalmol. Vis. Sci., 37(3), S324 (1996), Siegwart Jr., J. T., Invest. Ophthalmol. Vis. Sci., 37(3), S324 (1996)). Thus it is been shown possible to trigger irreversible stretching of the sclera in young rabbits by increasing the intraocular pressure but it is not possible to stretch the sclera in mature rabbits (Greene, P. R., ARVO Abstracts, 1978, p. 297). However, tests with reduction of the intraocular pressure by means of beta-blocking eye drops in humans developing myopia have no effect (Jensen, H., Acta, Ophthalmol., Suppl. 200, 69 (1991)).

There is no model for animal experiments which precisely corresponds to the human conditions. As mentioned above, it is possible to provoke myopia in some animals, e.g. cats and chicken, by sewing together the eye lids of newborn animals, but partly this experimental myopia develops much more rapidly than in humans, and partly the biological age of the animal (newborn) does not correspond to the same age when the myopia typically occurs in human (8–12 years). Furthermore, in chicken the sclera is considerably anomalous as it partly consists of cartilage.

As the conditions of the eye related to the refractory system is extremely common and preventive treatment is to be applied to children, probably during years of treatment, effective substances should be very safe. Accordingly, it would be a considerable improvement if a method for identification of a number of substances having an effect on the longitudinal growth of the eye was available. Among substances such identified, it would subsequently be possible to select, appropriate substances characterized by high efficiency and few side effects.

The present invention is related to methods for identification of substances or groups of substances being candidates for the treatment or prevention of disease of the eye related to the longitudinal growth of the eye.

One of the methods for identification of effective substances according to the present invention is related to the fact that, developmentwise, the retinal pigment epithelium is a part of the retina and forms an electrochemically active cell layer which is located between the choroid membrane of the eye and the neuronal part of the retina (neuroretina). It forms an electrically tight barrier and due to active ion transport (based on the $Na^+$-$K^+$ pump) it creates a difference in potential (the standing potential), the cornea-fundal potential, between the inner and the outer part of the eye of approximately 5 Mv.

Due to the anatomical conditions of the eye, this electrical field is in the nature of a dipole with + at the cornea and − at the back pole of the eye. The size and changes of the standing potential can thus be estimated with electrodes placed on each side of the eye by means of sideway movements of the eye. (EOG examination (electroocculography which is well known in the art).

The standing potential is furthermore positively correlated with the size of the socalled c-wave in ERG-recordings (electroretinography, which is well known in the art). According to one aspect of the present invention, the growth of the eye is related to the size and changes of the standing potential of the retinal pigment epithelium of the eye.

The transepithelial potential of the retinal pigment epithelium is maintained by a difference in ionic concentration between the cytoplasm of the pigment epithelial cell and the internal and external-surface. The state of the $Ca^{2+}$-channels determines intracellular $Ca^{2+}$. According to one aspect of the present invention, it is believed that substances affecting the state of $Ca^{2+}$ simultaneously affect the standing potential created by the retinal pigment epithelium. The state of the $Ca^{2+}$-channels may be determined by [$^3$H] ryanodine binding as the plant alkaloid ryanodine has been extensively used to study the functional interaction of the $Ca^{2+}$-release channel (Meissner G: Ryanodine receptor/$Ca^{2+}$ release channels and their regulation by endogenous effectors, Annu Rev Physiol 1994;56:485–508).

Accordingly, in a further aspect of the invention, the effect of different drugs on [$^3$H]-ryanodine binding can be used to screen for drugs that either strengthens the scleral connective tissue (increases the content of proteoglycans in sclera), or weakens it (decreases the content of proteoglycanes in sclera).

According to a still further theory behind the present invention, the biomechanical strength of the tissue is believed to be decisive for the stretching of the sclera rather than a change of the intraocular pressure as described in the prior art above. Substances increasing or decreasing the strength of the scleral tissue may be used according to the present invention for the treatment or prevention of disease relating to the longitudinal growth of the eye. In a further aspect, substances having a substantially selective effect on the posterior part of the sclera is preferred.

In a still further aspect of the present invention, substances having an effect on the content of proteoglycanes in the scleral tissue may be used for the treatment or prevention of disease relating to the longitudinal growth of the eye.

Connective tissue such as eg. sclera mainly consists of scattered cells in a base substance of proteoglycanes (proteins added to glycosaminoglycanes (branched polysaccharides)) and collagen fibres. The biomechanical properties of the tissue are determined by the content of these components and their organisation (Scott, J. E., Dermatan Sulphate Proteoglycans, Portland Press, 1993).

Furthermore, it has been demonstrated that fibroblasts in cell cultures may react to physiological electrical fields by taking on an oblong shape and orienting itself with the longitudinal axis orthogonally with the direction of the field (Erickson, C. A, et al., Cell Biol, Vol. 98, January 1984, 296–307). It has also been demonstrated that the connective tissue substance which is produced by fibroblasts may be determined by the shape of the cell (Evangilisti, R. et al, Eur. J. Histochem., 37, 161–172, 1993).

BRIEF DESCRIPTION OF THE PRESENT INVENTION

The present invention relates to a method for identification of substances which have an effect, either inhibiting or increasing, on the longitudinal growth of the human eye.

In another aspect, the invention relates to a method for treating and/or preventing myopia and hypermetropia and to pharmaceutical compositions for such treatment, as well as for use of substances for the preparation of medicaments useful for such treatment or prevention.

According to the present invention it is presumed that some of these substances act mainly on the retinal pigment epithelium and in addition on the receptors of the neuroretina.

In accordance with the present invention it is however believed, that the substances in tha last end excerts the treating or preventing effect through an effect on the ion transport in and out of the cell in the retinal pigment epithelium and thereby exerts its effect on the longitudinal growth of the eye.

In one aspect the invention comprises screening of an optional number of substances for the effect on the metabolical activity in the retinal pigment epithelium of the eye.

This effect may be measured by different methods. One of these methods relates to the activation of the $Ca^{2+}$-release channel. This $Ca^{2+}$-release channel may be influenced by different effectors on receptors on the cell membrane. Examples of such receptors are the ryanodine receptor (RyR) and the inositol triphosphate ($IP_3$) receptor.

In another aspect, the present invention relates to the surprising finding that substances affecting the size of the standing potential are useful for the treatment or prevention of abnormal growth of the axial length of the eye.

Accordingly, by measuring of effect of the substances on the electrochemical potential over the retinal pigment epithelium, the so-called "standing potential", or the effect on the so-called "c-wave" by electro retinography (ERG), suitable substances for treating or preventing conditions related to the longitudinal growth of the eye are easily identified.

Substances increasing the standing potential or c-wave will inhibit the longitudinal growth of the eye and will thus be applicable for treatment of myopia. Substances reducing the standing potential or c-wave will increase the longitudinal growth of the eye and will thus be applicable for treatment of hypermetropia.

In a further aspect of the invention it is believed that physiological electrical fields are important in relation to the extracellular matrix of the scleral tissue and thereby to the biomechanical properties of sclera. An increase of the electrical field is believed to influence the connective tissue cells in the sclera to take on an oblong form and deposit orthogonally on the field, i.e. in the longitudinal direction of the sclera, making the tissue organise more appropriately as concerns content of base substance and packing of collagen fibres. After long time treatment the sclera will be more resistant to draft and thus less likely to give in to the intraoccular pressure, thus avoiding development of myopia.

In a further aspect of the invention, substances affecting the composition of the proteoglycanes may be used for the treatment of abnormalities of the longitudinal growth of the eye.

In a further aspect, the invention comprises a method involving analysis of sclera tests from test animals after treatment (0–6 months) with substances influencing the sclera. Accordingly, the method comprises identifying one or more of the following elements: the effect of the substance on the proteoglycanes; the distribution between various glycosaminoglycane types; and the content of collagen specific amino acids. The analysis may additionally comprise identifying the density of collagen fibrils and the distribution between various fibrils diameters by means of electron microscopy.

According to the present invention, it is possible that the effect on the composition of the proteoglycanes and/or the collagen specific amino acid present in the connective tissue of the sclera of the eye is due to an influence on the metabolical activity in the retinal pigment epithelium of the substance of the eye.

Substances increasing the content of proteoglycanes and collagen specific amino acids will strengthen the connective tissue in the sclera, reduce the longitudinal growth of the eye and thus work against myopia. Substances increasing the content of dermatane sulphate in proportion to the other glycosaminocglycanes will furthermore strengthen the connective tissue in the sclera and work against myopia. Substances increasing the density of collagen fibrils and increasing the diameter of the fibrils will furthermore strengthen the connective tissue in the sclera and work against myopia.

Substances reducing the content of proteoglycanes and collagen specific amino acids will weaken the connective tissue in the sclera, increase the longitudinal growth of the eye and thus work against hypermetropia. Substances reducing the content of dermatane sulphate in proportion to the other glycosaminoglycanes will weaken the connective tissue in the sclera and work against hypermetropia. Substances reducing the density of collagen fibrils and reducing the diameter of the fibrils will furthermore weaken the connective tissue in the sclera and work against hypermetropia.

In a further aspect, the invention relates to a method for identifying substances affecting the composition of the proteoglycanes of the sclera of the eye, and thereby exert an effect of the strength of the connective tissue.

BRIEF DESCRIPTION OF THE FIGURES

FIG. 3 shows the general formula of xanthine and of three derivatives thereof, caffeine, theophylline and theobromine, respectively. As appears from the figure, caffeine and theobromine are substituted in position 7 by a methyl group.

FIG. 12 shows the correlation between the effect of different methylxanthines on the content of proteoglycanes in posterior sclera and the effect of the same methylxanthines on [$^3$H] ryanodine binding capacity compared to that of the control, xanthine, The values appears from Table 13. Caffeine is represented by 1,7-dimethylxanthine since this is the most dominating metabolite in serum of rabbits after feeding with caffeine. As appears from the figure, a $^3$H ryanodine binding exceeding 130% compared to xanthine seems to be needed to produce a positive effect on the content of proteoglycanes in sclera.

Figure 1:
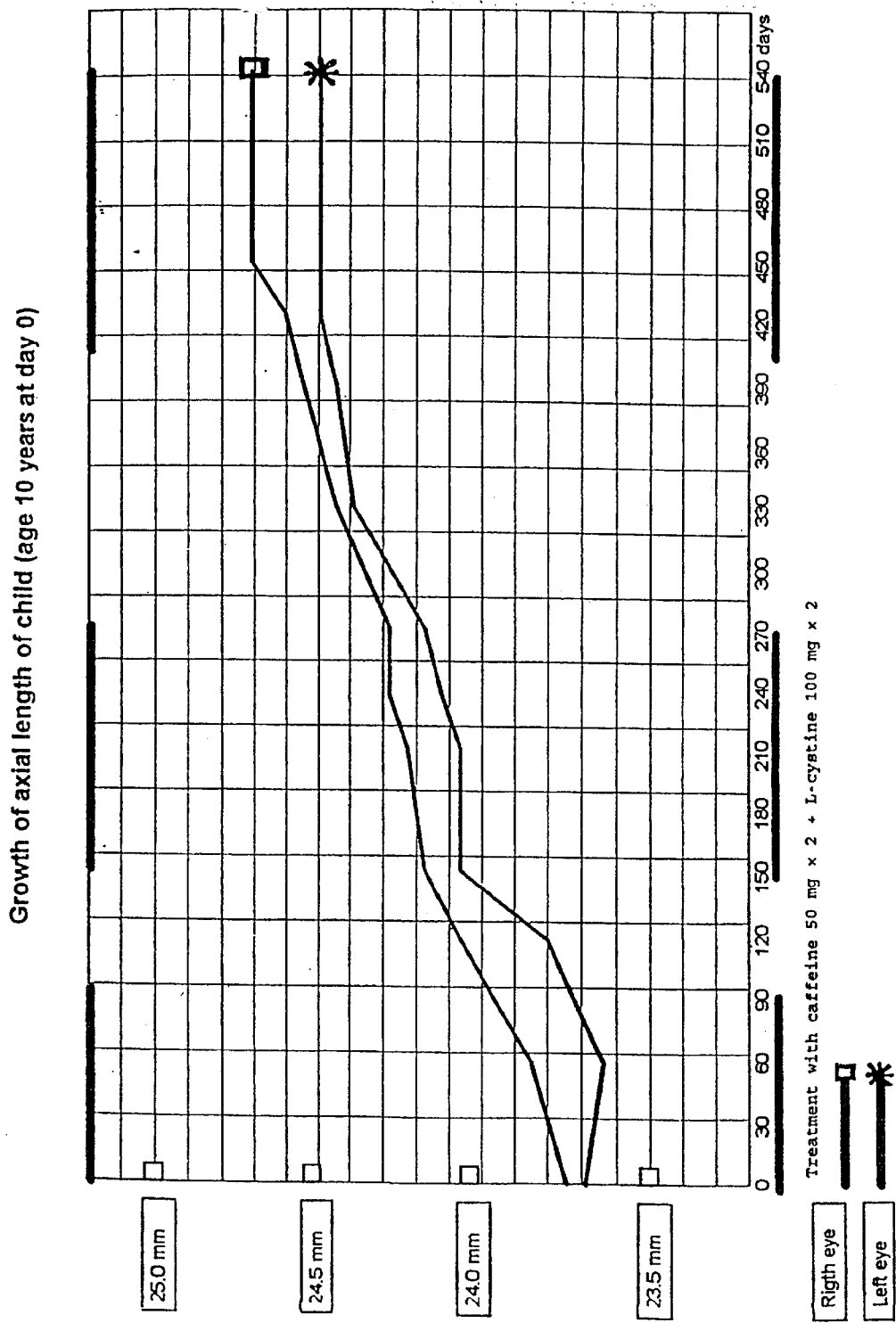
FIG. 1 shows the inhibiting effect of a combination of caffeine and L-cystine on the longitudinal growth of the human eye.
Figure 2:
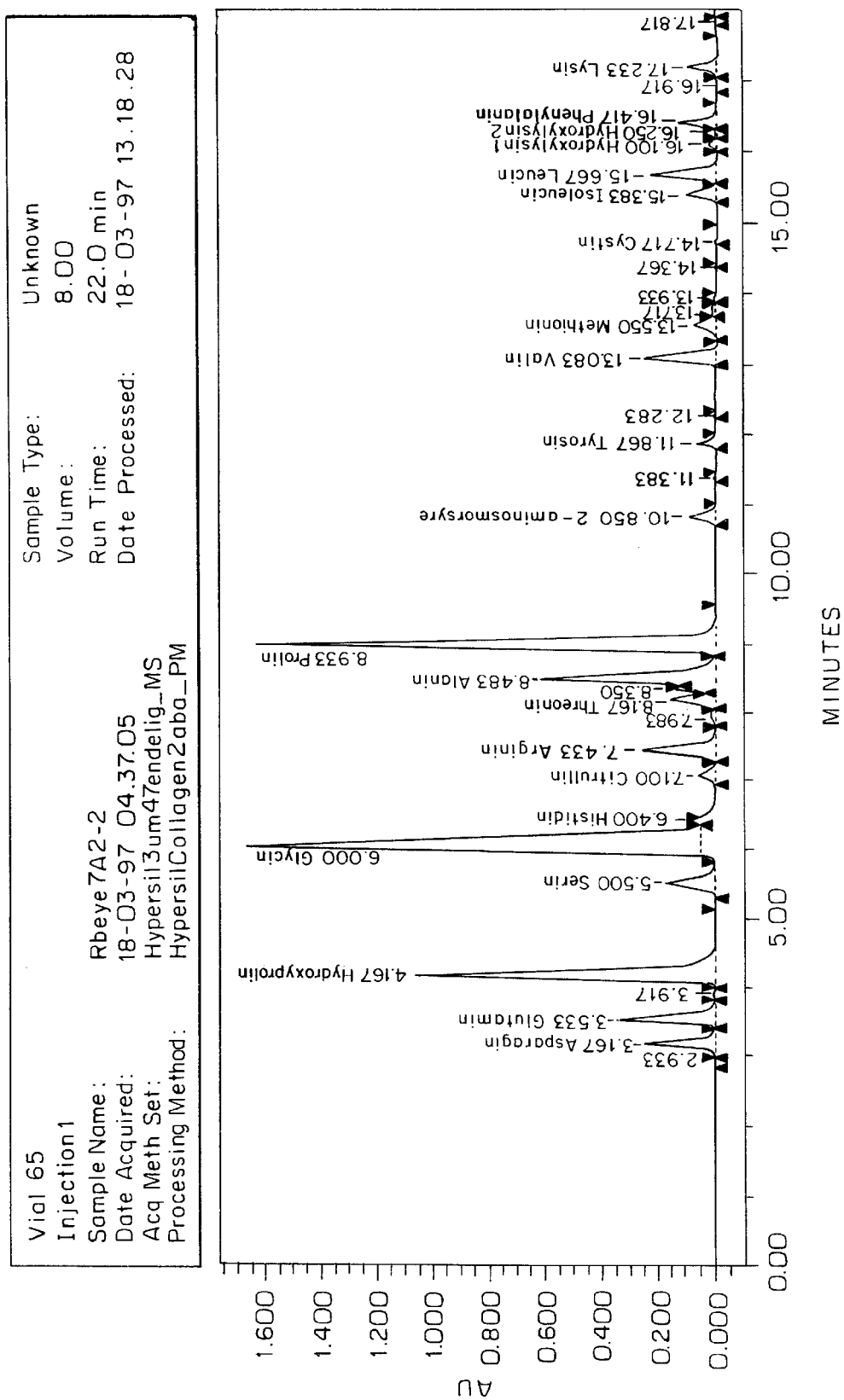
FIG. 2 shows an example of an analysis curve for amino acids by the application of HPLC.
Figure 4:
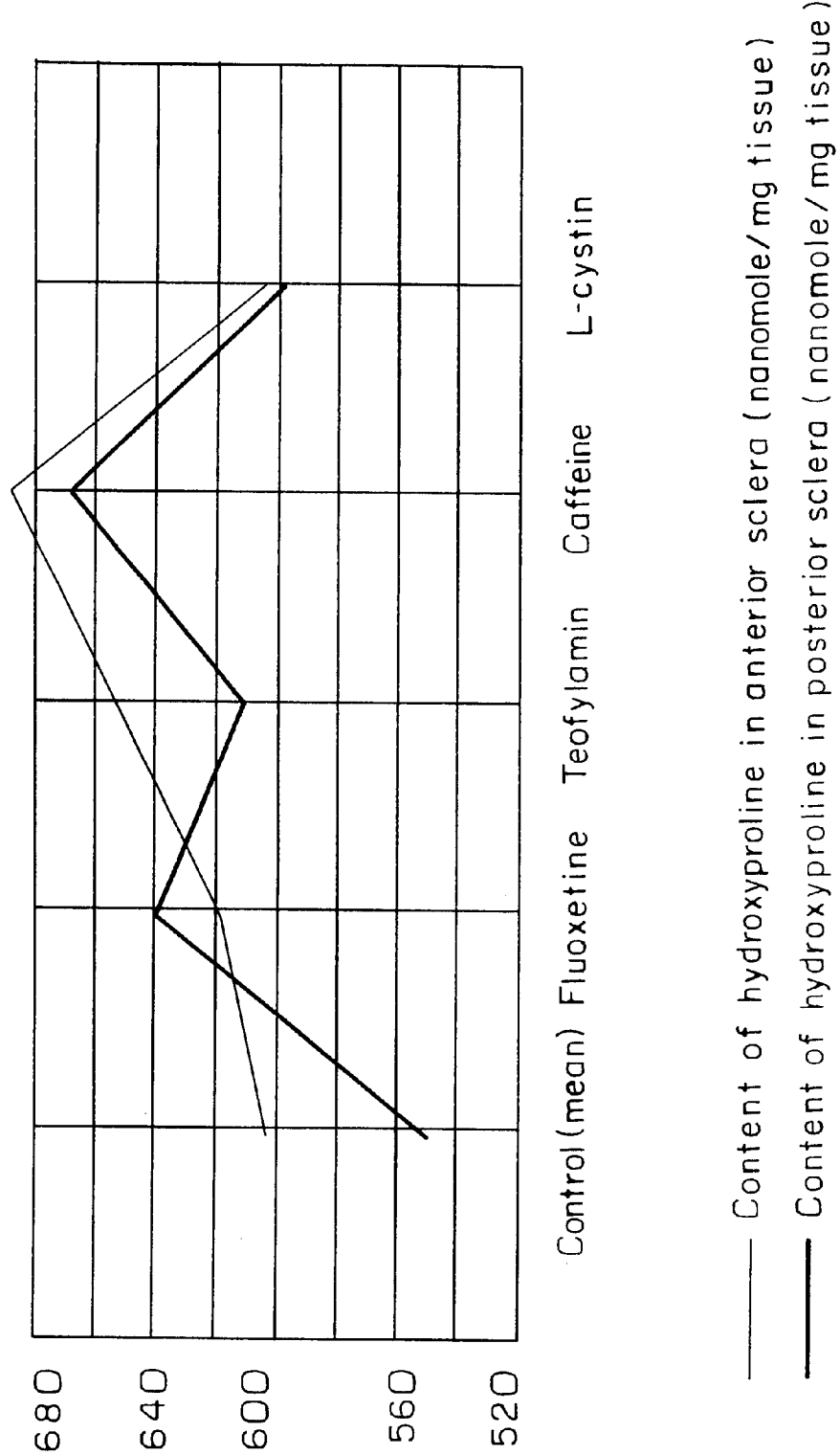
FIG. 4 shows the content of hydroxyproline in anterior and posterior sclera after treatment with the substances described in Example 2.
Figure 5:
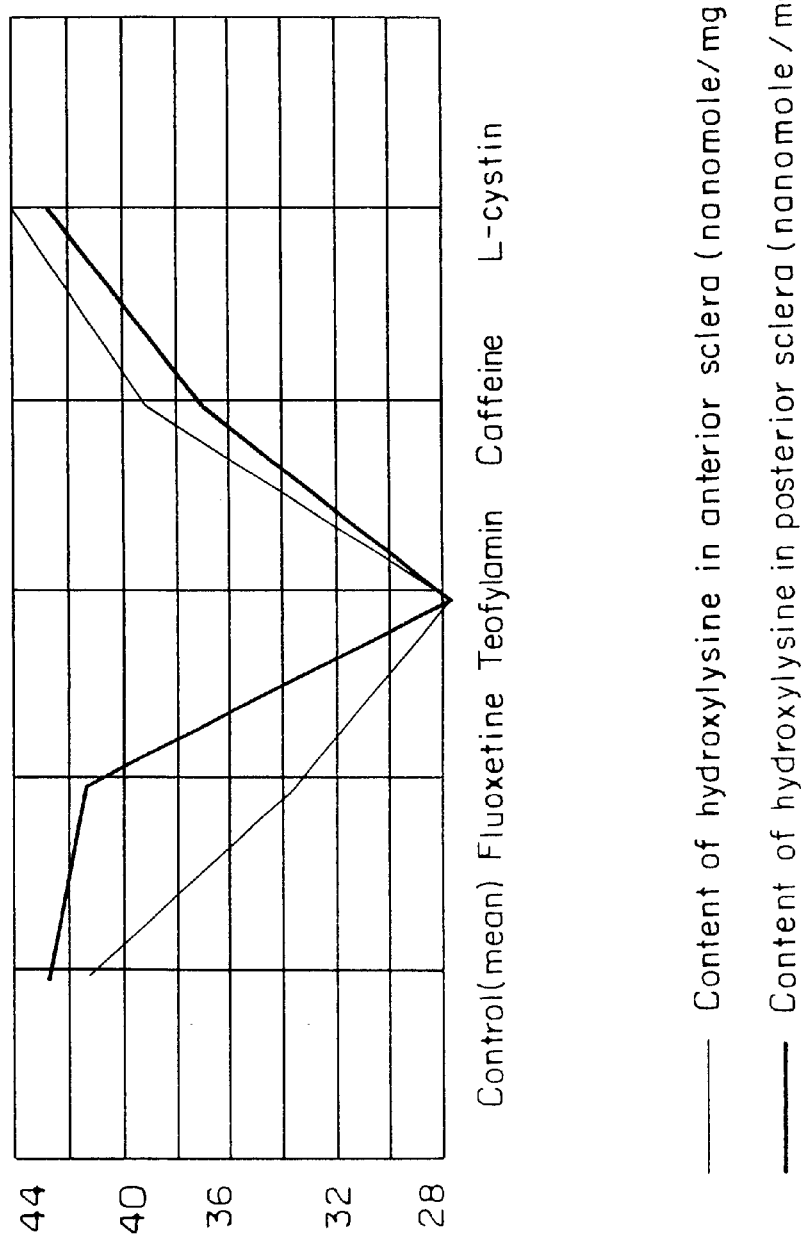
FIG. 5 shows the content of hydroxylysine in anterior and posterior sclera after treatment with the substances described in Example 2.
Figure 6:
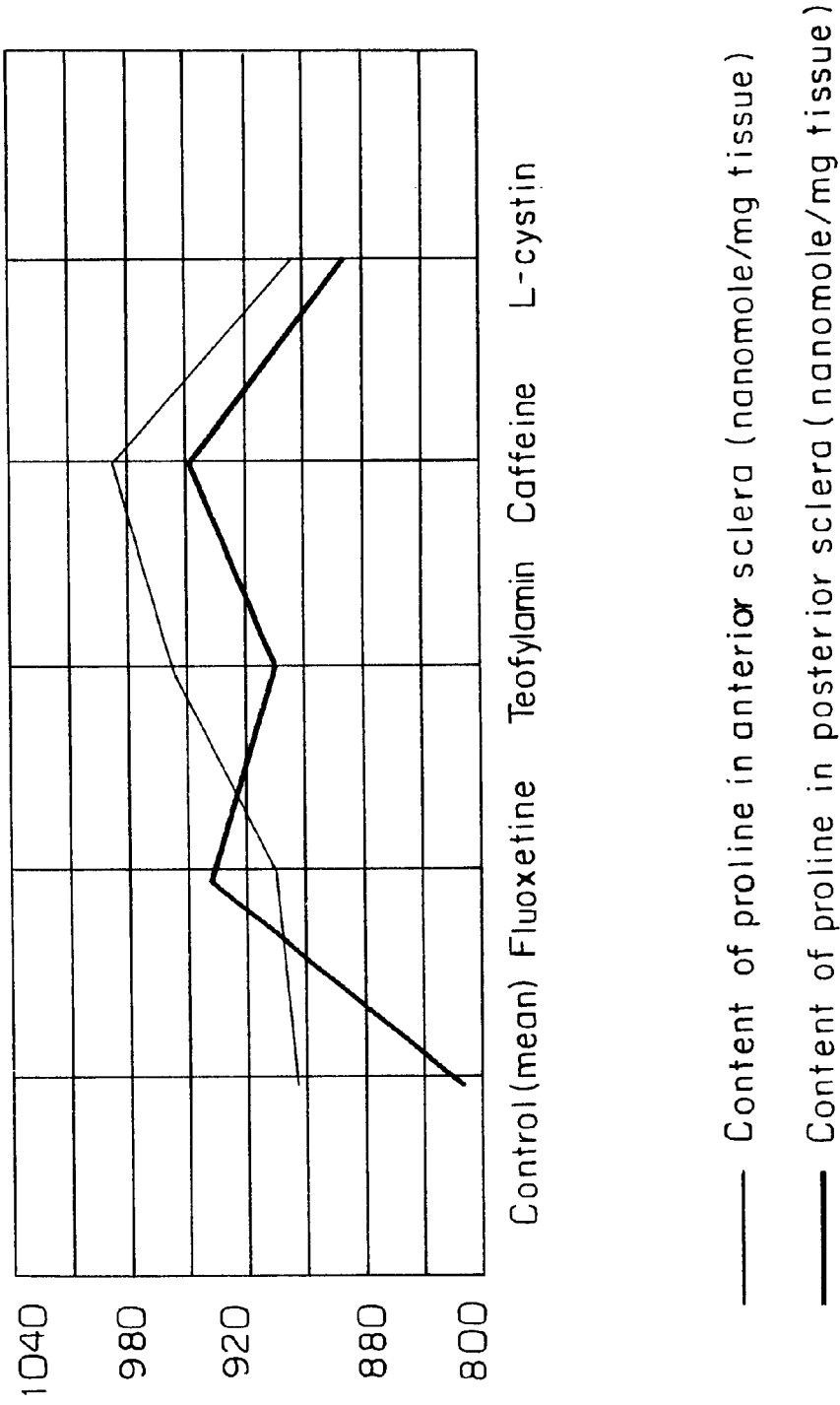
FIG. 6 shows the content of proline in anterior and posterior sclera after treatment with the substances described in Example 2.
Figure 7:
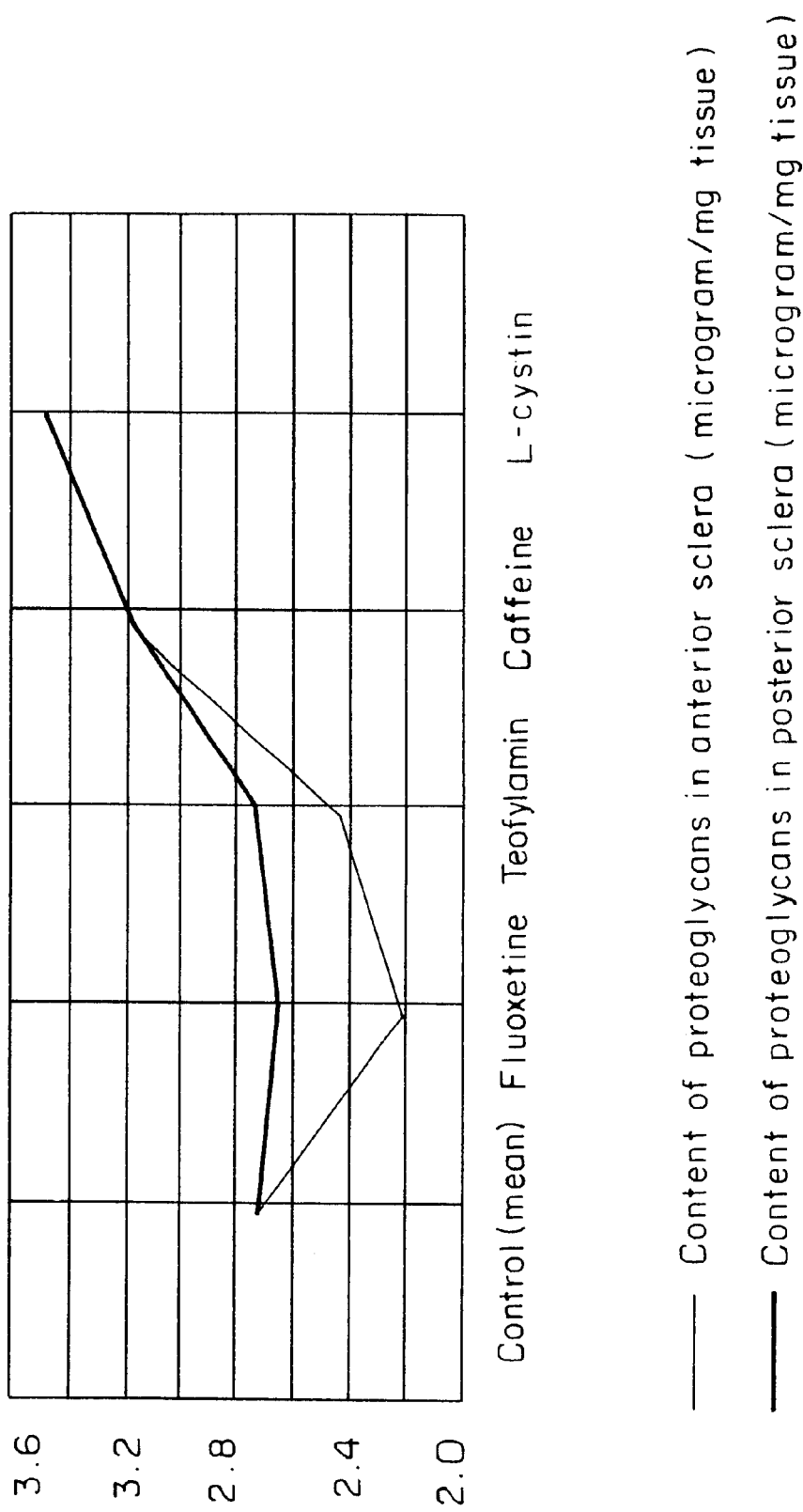
FIG. 7 shows the content of proteoglycanes in anterior and posterior sclera after treatment with the substances described in Example 2.
Figure 8:
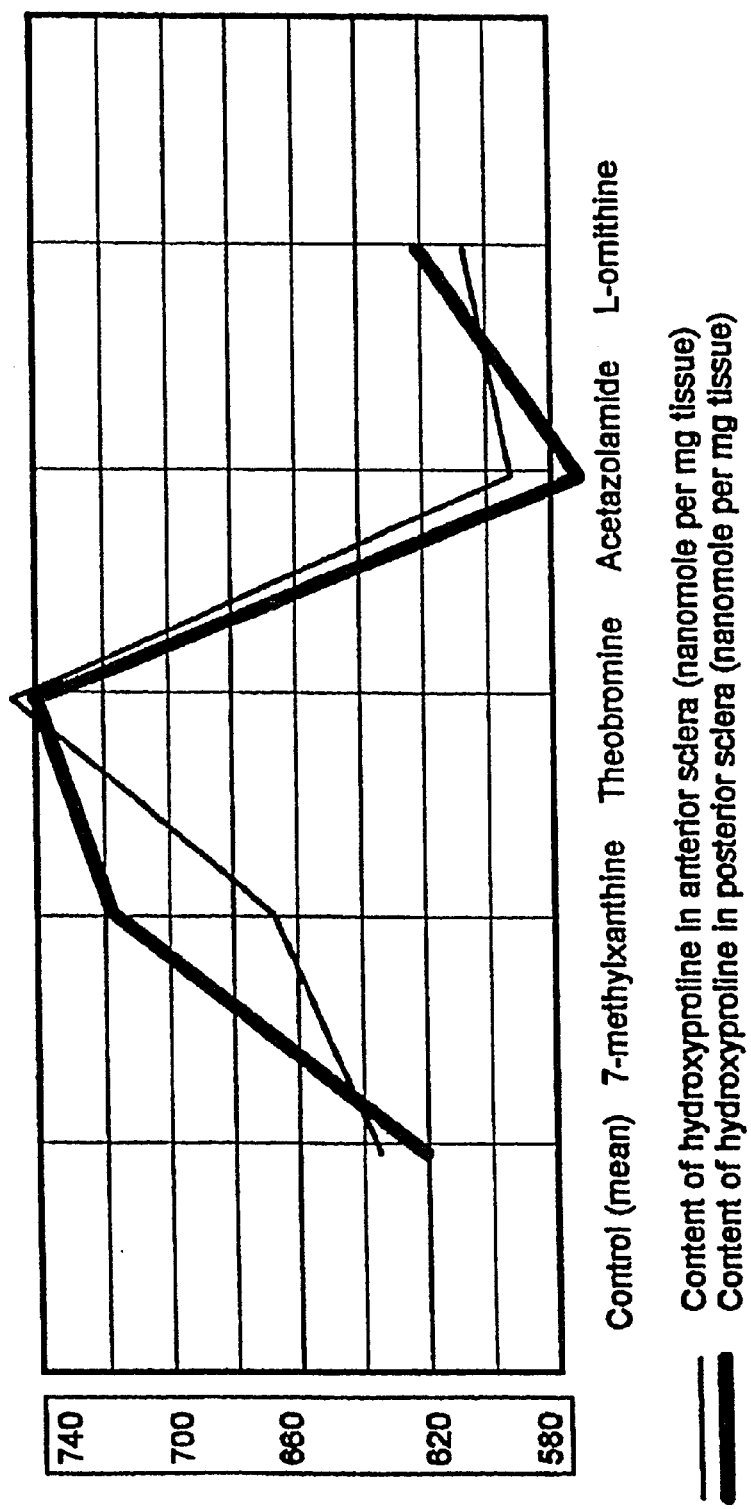
FIG. 8 shows the content of hydroxyproline in anterior and posterior sclera after treatment with the substances described in Example 4.
Figure 9:
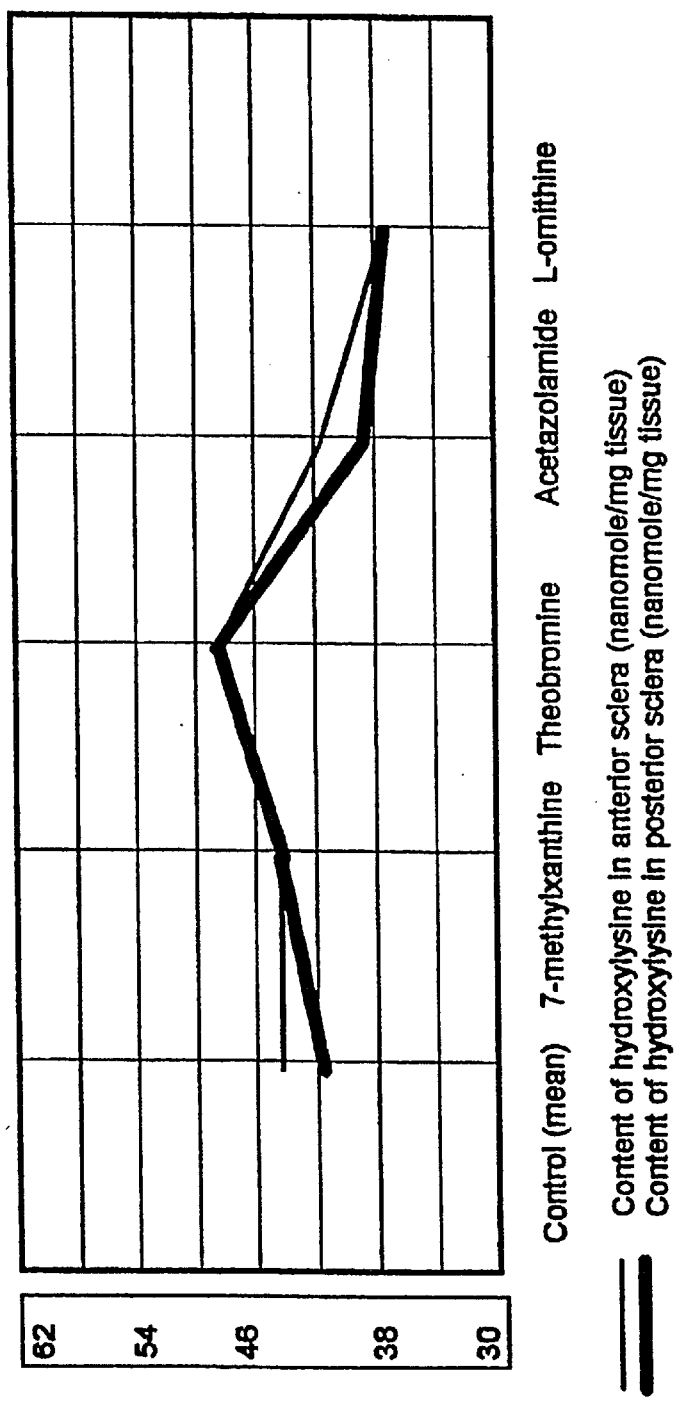
FIG. 9 shows the content of hydroxylysine in anterior and posterior sclera after treatment with the substances described in Example 4.
Figure 10:
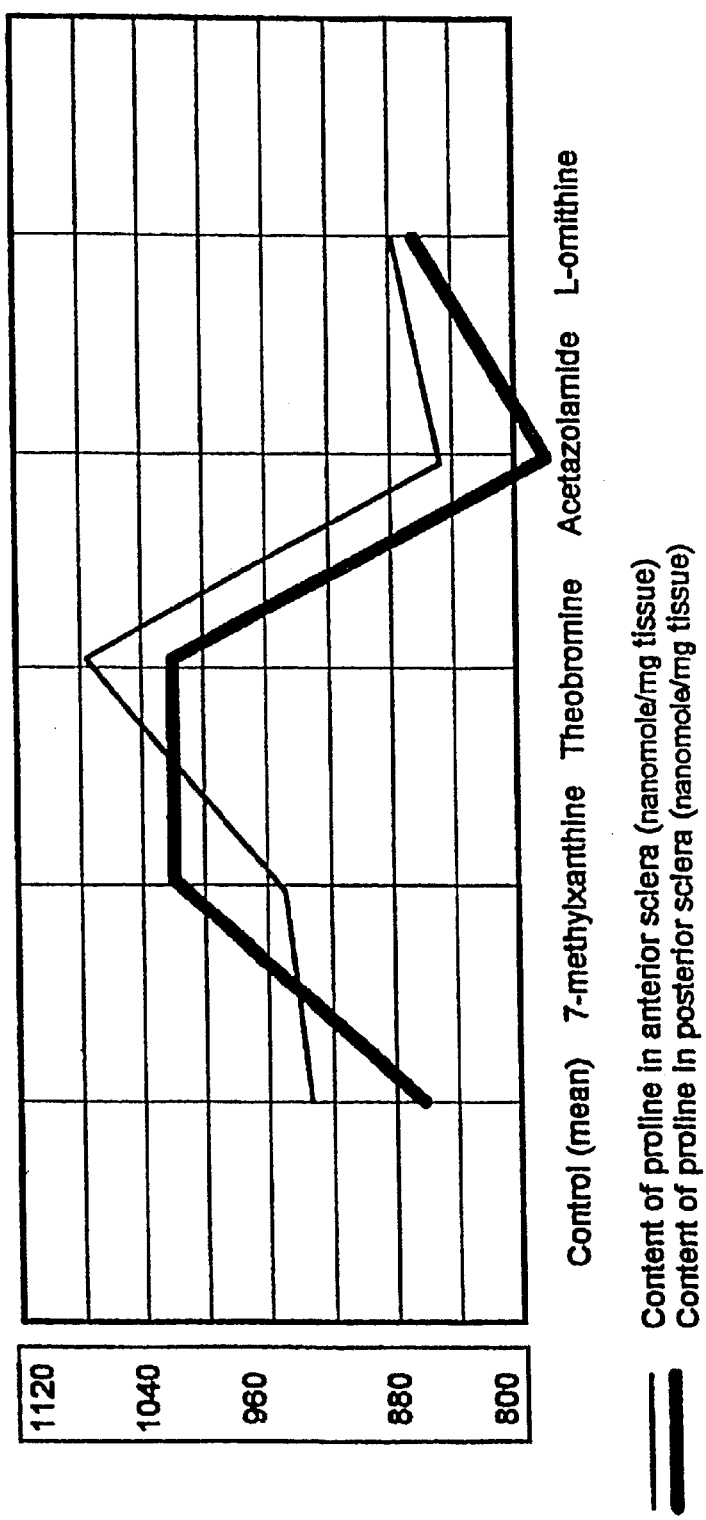
FIG. 10 shows the content of proline in anterior and posterior sclera after treatment with the substances described in Example 4.
Figure 11:
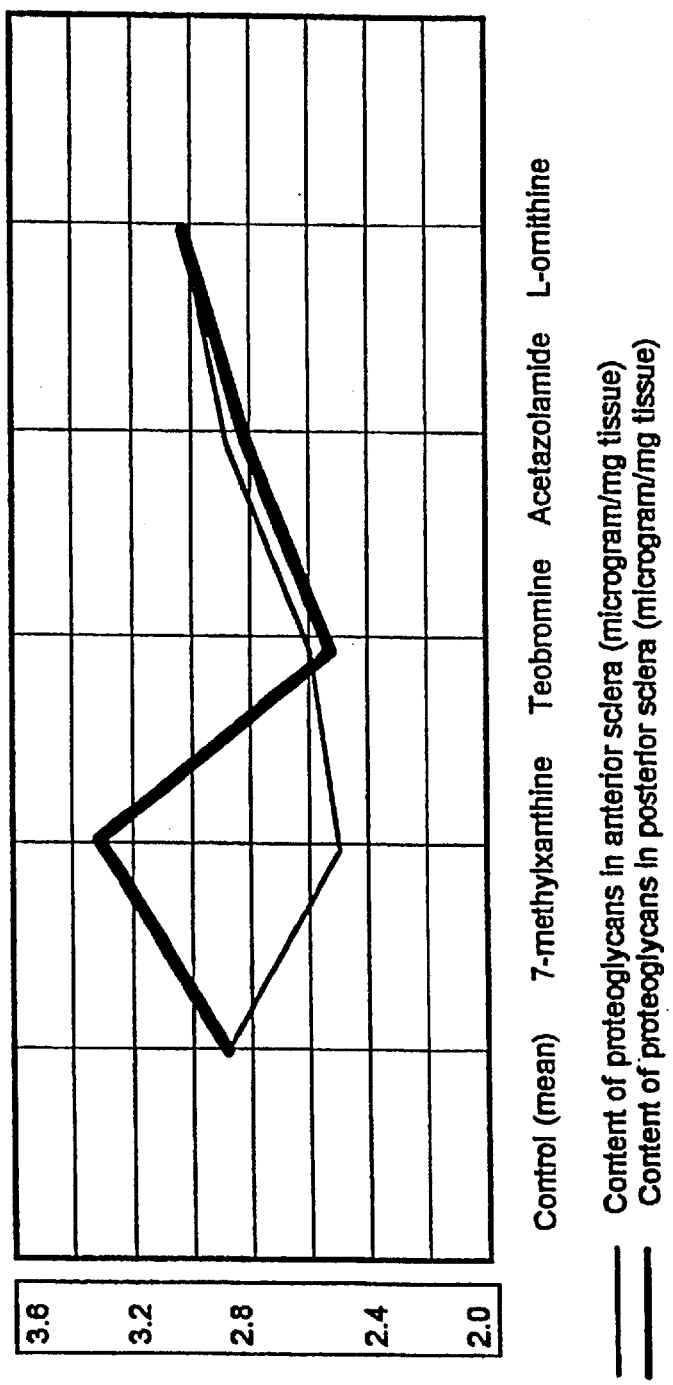
FIG. 11 shows the content of proteoglycanes in anterior and posterior sclera after treatment with the substances described in Example 4.

Interesting embodiments of the aspects of the invention appear from the appended claims.

DETAILED DESCRIPTION OF THE INVENTION

The present invention applies the surprising finding that substances which have an increasing effect on the standing potential or c-wave of the eye by ERG will increase the scleral connective tissues ability to resist abnormal growth or stretching, and thus work against development of myopia. The increased resistant may according to the present invention be due to increase in the content of proteoglycanes and/or collagen specific amino acids such as hydroxyproline, hydroxylysine and proline. Furthermore, an increase in the diameter of the collagen fibrils may also contribute to the effect according to the invention.

It is furthermore believed that the specific glycosaminoglycanes of the proteoglycanes may have an effect on the structure so that an increased proportion of e.g the content of dermatane sulphate in percentages is related to increased mechanical strength of the sclera and thus also work against development of myopia. Similarly, a decrease works against development of hypermetropia In a further embodiment, the invention applies the surprising finding that substances which reduce the standing potential or c-wave of the eye by ERG will, in similarity, reduce the content of proteoglycanes and/or collagen specific amino acids, reduce the content of dermatane sulphate in percentages, reduce the diameter of the collagen fibrils, and thus reduce the scleral connective tissues ability to resist stretching, and thus reduce the level of hypermetropia.

In order to examine whether a substance is able to produce a change in the connective tissue substance of the sclera, it is normally necessary to treat test animals for a long time, presumably several months. Therefore it would be very resource consuming to test a large number of substances by means of this method alone. By confining oneself to testing substances which influence the standing potential or c-wave of the eye by ERG, it becomes much more likely to identify substances which with few or no side effects are able to influence the scleral connective tissue and thus be applicable for treatment of myopia or hypermetropia.

As will be described in the following, the invention further relates to the surprising finding, that substances effecting the metabolic state of the cells of the retinal pigment epithelium are also able to induce the effects described above. This effect may by detected indifferent ways, such as by the state of the $Ca^{2+}$-channels. In addition, the state of the $Ca^{2+}$-channels may be determined by $[^3H]$ ryanodine binding, or in another preferred embodiment of the present invention, by the inositol triphosphate ($IP_3$) receptor. Inositol triphosphate increase intracellular calcium.

Accordingly, substances binding to the receptors and thereby results in an increase in the intracellular calcium ions may be utilized for the treatment of myopia, and substances which inhibit the receptors may be used in the treatment of hypermetropia in accordance with the teaching of the present invention.

The method according to the invention for screening substances effective of treating disorders of the eye related to the axial length of the eye comprises identifying substances having an effect on the retinal pigment epithelium. It is believed that substances having an effect on the more primitive pigment epithelium and a rather limited effect on neural tissue will result in a treatment having less side effects compared to the use of substances having a substantial effect on the central nervous system.

Accordingly, the present invention in a still other aspect relates to the use of substances wherein the effect on the pigment epithelium is primarily on the ion exchange over the cell membrane. This effect may be regarded as a metabolic effect. Accordingly, in a further aspect of the invention, the method is for screening substances effective of treating disorders of the eye related to the axial length of the eye and comprises identifying substances having an effect substantially on the pigment epithelium compared to the effect on the neuroretina.

The present invention relates in its broad definition to a method for screening substances effective of treating disorders of the eye related to the axial length of the eye. The method essentially comprises the identification of substances having an effect on the retinal pigment epithelium of the eye as this effect on the retinal pigment epithelium has a clear connection to the function of the control of the axial growth of the eye.

As the function of the retinal pigment epithelium is possibly also affected by a direct or receptor effect on neuroretina, the effect on the retinal pigment epithelium may be through an effect of the substance on the neuroretina. In a further aspect of the invention, the substance may have an effect directly on the neuroretina together with a direct effect on the retinal pigment epithelium. In a further aspect the effect on the neuroretina also induces an effect on the retinal pigment epithelium.

The ion exchange pumping on the cell membrane is, driven by cAMP. An effect of a substance to be screened may exert an inhibiting or increasing effect on the pump and thereby on the function of the retinal epithelium. In other words it could be expressed by the fact that the substances to be screened are selected by the metabolic effect of the substance on the pigment epithelium.

One preferred method according to the invention is to identify the effect on the pigment epithelium by means of the standing potential and/or on the c-wave by electro retinography (ERG). In a further aspect, also the effect on the a-wave and/or on the b-wave in the neuroretina is measured whereby it is possible to identify substances having an effect substantially on the retinal pigment epithelium compared to an effect on the neuroretina where the latter is shown as an effect on the a-wave and/or on the b-wave.

In order to identify substances effective of inhibiting the is longitudinal growth of the eye, substances increasing the standing potential and/or the c-wave are selected. These substances may be used for the treatment or prevention of myopia.

In order to identify substances effective of increasing the longitudinal growth of the eye, substances decreasing the standing potential and/or the c-wave are identified. These substances may be used for the treatment or prevention of hypermetropia.

In a further embodiment of the invention a method for screening substances effective of treating disorders of the eye related to the axial length of the is eye disclosed. The method comprises identifying substances having an effect on the composition of the proteoglycanes and/or the collagen specific amino acid present in the connective tissue of the sclera of the eye.

This method may in one embodiment be by treating an animal with the substance and measuring the effect on the composition of the connective tissue of the sclera.

In another embodiment the method comprises adding the substance to a tissue culture comprising retinal pigment epithelium and fibroblasts and identify the impact of the substance on the production and composition of the proteoglycanes and/or the collagen specific amino acid produced by the fibroblasts in the tissue culture.

The method according to the invention also comprises identifying substances effective of inhibiting the longitudinal growth of the eye. These substances are such substances which increase the content of proteglycanes of the sclera, and may be used for the treatment or prevention of myopia.

Accordingly, substances effective of increasing the longitudinal growth of the eye are the substances decreasing the content of proteoglycanes of the sclera. These substances may be used for the treatment or prevention of hypermetropia.

The effect of the substance on the proteoglycanes can generally be identified within a period from as early as 1 day to about 12 weeks from the start of the treatment. However, normally at least one week of treatment is necessary for having an effect which can be measured with the existing analytical methods.

To apply an animal model to a human effect, it is generally preferred that the test animal is a mammal. However other animals such as birds and reptiles may employed in the present method.

As is evident for the above explanation, and due to the surprising finding that an effect on the retinal pigment epithelium may be utilized for treatment of disorders of the axial length of the eye, any substance may be subjected to the method according to the invention.

In one embodiment the invention relates to the screening of a substance selected from the group consisting of prostaglandine and analogues thereof and compounds of the general formula I, II or III

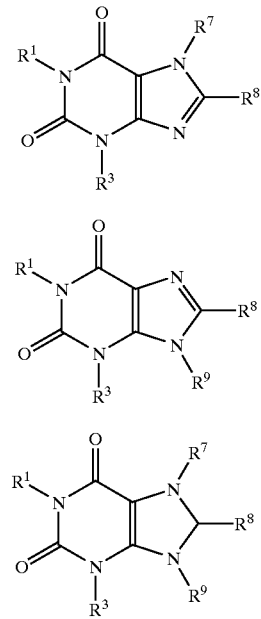

wherein $R^1$, $R^3$, $R^7$, and $R^9$ are independently selected from the group consisting of hydrogen, optionally substituted $C_{1-20}$-alkyl, optionally substituted $C_{2-20}$-alkenyl, optionally substituted $C_{4-20}$-alkadienyl, optionally substituted $C_{6-20}$-alkatrienyl, optionally substituted $C_{2-20}$ alkynyl, optionally substituted $C_{1-20}$-alkoxycarbonyl, optionally substituted $C_{1-20}$-alkylcarbonyl, formyl, optionally substituted aryl, optionally substituted aryloxycarbonyl, optionally substituted arylcarbonyl, optionally substituted heteroaryl, optionally substituted heteroaryloxycarbonyl, optionally substituted heteroarylcarbonyl, carbamoyl, mono- and di($C_{1-20}$-alkyl)aminocarbonyl, mono- and di($C_{1-20}$-alkyl)amino-$C_{1-20}$-alkyl-aminocarbonyl, and halogen such as fluoro, chloro, bromo or iodo, and $R^8$ is selected from the group consisting of hydrogen, optionally substituted $C_{1-20}$-alkyl, optionally substituted $C_{2-20}$-alkenyl, optionally substituted $C_{4-20}$-alkadienyl, optionally substituted $C_{6-20}$-alkatrienyl; optionally substituted $C_{2-20}$-alkynyl, optionally substituted $C_{1-20}$-alkoxy, optionally substituted $C_{2-20}$-alkenyloxy, carboxy, hydroxy, optionally substituted $C_{1-20}$-alkoxycarbonyl, optionally substituted $C_{1-20}$-alkylcarbonyl, formyl, optionally substituted aryl, optionally substituted aryloxycarbonyl, optionally substituted aryloxy, optionally substituted arylcarbonyl, optionally substituted arylcarbonyl, optionally substituted heteroaryl, optionally substituted heteroaryloxycarbonyl, optionally substituted heteroaryloxy, optionally substituted heteroarylcarbonyl, amino, mono- and di($C_{1-20}$-alkyl) amino, carbamoyl, mono- and di($C_{1-20}$-alkyl) aminocarbonyl, amino-$C_{1-20}$-alkylaminocarbonyl, mono- and di($C_{1-20}$-alkyl)amino-$C_{1-20}$-alkylaminocarbonyl, optionally substituted $C_{1-20}$-alkylcarbonylamino, guanidino, carbamido, optionally substituted $C_{1-20}$-alkanoyloxy, sulphono, optionally substituted $C_{1-20}$-alkylsulphonyloxy, nitro, sulphanyl, optionally substituted $C_{1-20}$-alkylthio, and halogen such as fluoro, chloro, bromo or iodo.

Preferably, $R^1$, $R^3$, $R^7$, and $R^9$ are independently selected from the group consisting of.hydrogen, optionally substituted $C_{1-6}$-alkyl, optionally substituted $C_{2-6}$-alkenyl, optionally substituted $C_{2-6}$-alkynyl, optionally substituted $C_{1-6}$-alkylcarbonyl, formyl, optionally substituted aryl, optionally substituted arylcarbonyl, optionally substituted heteroaryl, and optionally substituted heteroarylcarbonyl, and $R^8$ is selected from the group consisting of hydrogen, optionally substituted $C_{1-6}$-alkyl, optionally substituted $C_{2-6}$-alkenyl, optionally substituted $C_{2-6}$-alkynyl, optionally substituted $C_{1-6}$-alkoxy, optionally substituted $C_{2-6}$-alkenyloxy, carboxy, hydroxy, optionally substituted $C_{1-6}$-alkoxycarbonyl, optionally substituted $C_{1-6}$-alkylcarbonyl, formyl, optionally substituted aryl, optionally substituted aryloxycarbonyl, optionally, substituted aryloxy, optionally substituted arylcarbonyl, optionally substituted arylcarbonyl, optionally substituted heteroaryl, optionally substituted heteroaryloxycarbonyl, optionally substituted heteroaryloxy, optionally substituted heteroarylcarbonyl, amino, mono- and di($C_{1-6}$-alkyl) amino, carbamoyl, mono- and di($C_{1-6}$-alkyl) aminocarbonyl, optionally substituted $C_{1-6}$-alkylcarbonylamino, guanidino, carbamido, optionally substituted $C_{1-6}$-alkanoyloxy, sulphono, optionally substituted $C_{1-6}$-alkylsulphonyloxy, nitro, sulphanyl, optionally substituted $C_{1-6}$-alkylthio, and halogen such as fluoro, chloro, bromo or iodo.

In a further embodiment, $R^1$, $R^3$, $R^7$ and $R^9$ are independently selected from the group consisting of hydrogen, optionally substituted $C_{1-6}$-alkyl, optionally substituted $C_{2-6}$-alkenyl, optionally substituted $C_{2-6}$ alkynyl, optionally substituted aryl, and $R^8$ is selected from the group consisting of hydrogen, optionally substituted $C_{1-6}$-alkyl, optionally substituted $C_{2-6}$-alkenyl, optionally substituted $C_{2-6}$-alkynyl, optionally substituted $C_{1-6}$-alkoxy, optionally substituted $C_{2-6}$-alkenyloxy, carboxy, hydroxy, optionally substituted aryl, optionally substituted aryloxy, optionally substituted heteroaryl, optionally substituted heteroaryloxy, optionally substituted heteroarylcarbonyl, amino, nitro, sulphanyl, and halogen such as fluoro, chloro, bromo or iodo.

In a further embodiment the invention relates to the screening of a substance selected from the following group of substances selected based on different criteria with respect to inhibiting or stimulating effects known from the litterature. The group comprises prostaglandine and analogues thereof such as F2 alpha analogues including PhXA41, prostaglandin receptor agonists including PGF 2 alpha, 17-phenyl trinor PGE2, and U46619; adenosine A2-receptor agonists such as 5'(N-ethyl)-carboxamido adenosine, alpha-2D adrenergic receptor agonists and antagonists; alpha -2-adrenergic agonist such as UK-14,304; prostaglandin agonists such as 16-phenoxy-PF2 alpha, cloprostenol, 17-phenyl-PGF2 alpha, fluprostenol, and PhXA85; insulin; bumetanide, petides such as bradykinin, arginine vasopressin, bombesine, substance P, pituitary adenylate cyclase activating polypeptide, atrial natriuretic peptide, somatostatin analogues such as Tyr11-somatostatin-14, Leu8, D-Trp22, and Tyr25-somatostatin-28; muscarine receptor agonists and antagonists such as the Carbachol (stimulates production of inositolphosphate by way of M3 muscarinic receptors), 4-diphenylacetoxy-N-methylpiperadine methiodide, atropin and pirencepine (blocking the effect); calcittiol receptor agonist and antagonists, acetylcholin (increases introcellular calcium by inositol triphosphate receptors), nonsteroidal antiinflammatory drugs such as niflumic acid; Thapsigargin; A23187; phosphodiesterase inhibitors such as rolipram and zaprinast, 4-chloro-3-ethylphenol; Bastidin; Veratridine; estrogens and derivatives thereof; Tamoxifen; and Bay K 8644 (1,4-Dihydro-2,6-dimethyl-5-nitor-4-(2(triflouromethyl)-phenyl)-3-pyridinencarboxylic acid methyl ester.

Upon screening, substances selected due their ability of treating myopia or hypermetropia based on the criteria defined in the present text may be used for the preparation of a medicament for treating or preventing disorders of the eye related to the axial length of the eye for a method for treating or preventing the disorder by administration of a pharmaceutically effective amount of the substance to an individual in need thereof.

In a further embodiment, the present invention relates to a method for treating and/or preventing myopia of a human eye comprising administering to an individual in need thereof a therapeutically effective amount of one or more substances selected from caffeine; 1,7-dimethylxanthine (paraxanthine), 7-methylxanthine (heteroxanthine), isobutylntethylxanthine (IBMX) and derivatives; 3-methylxanthine, 1-methylxanthine, 1-Hexyl-3,7-dimethylxanthine (pentifylline); 1,7-Dimethyl-xanthine; 1,3-Dipropyl-7-methyl-xanthine; 7-Propylxanthine; 7β-Chloroethyl-1,3-dimethylxanthine; 3,7-Dimethyl-1-propargyl-xanthine; 3-Propylxanthine; 1-(5-Oxohexyl)-3,7-dimethylxanthine (pentoxyfylline); 3-Isobutyl-1-methylxanthine; 3,9-Dimethylxanthine 8-Cyclopentyl-1,3-dimethylxanthine; 1,3-Bis(3-methylbut-2-butenyl-7-methylxanthine; 3,7-Dihydro-7-methyl-1,3-dipropyl-1H-purine-2,6-dione; 7-Methyl-1,3-diprenylxanthine(7-methyl-1,3-dipropyl-xanthine; 7-Ethoxymethyl-1-(5-hydroxy-5-methylhex-methylxanthine (Torbafylline, "HWA 448"); 1-(5 hydoxy-5-methylhexyl)-3-methyl-7-propylxanthine (A 80.2715); 3,7-Dimethyl-1-(5-oxyhexyl)-xanthine (Pentoxifylline, "Trental");3,7-Dimethyl-1-(5-hydroxyhexyl)-xanthine (Hydroxypentoxifylline); 1-Hexyl-3,7-dimethylxanthine (Pentifylline, "Cosaldon"); 3,7-Dimethyl-1-proparglyxanthine (DMPX); (E)-8-(3,4-Dimethoxystyryl)-1,3-dipropyl-7-methylxanthine (KF 17837)(Lisofylline); 1-(5-Hydroxy-5-methylhexyl)-3-methylxanthine (Albifylline, "HWA 138"): 3-Methyl-1-(5'-oxohexyl)-7-propylxanthine (Propentofylline, "HWA-285"); 1-(5-Hydroxyhexyl)-3,7-dimethylxanthine (BL 194); (E)-1,3-dipropyl-8-(3,4-dimethoxystyryl)-7-methylxanthine (KF 17.837); 1,3-di-n-butyl-7-(2'oxopropyl)-xanthine (Denbufylline); 1-n-butyl-3-n-propylxanthine (XT-044); 7-(2,3-dihydroxypropyl)-theophylline (Dyphylline); 7-Methyl-8-(2-hydroxy-N-methylethylamino)-theophylline (Cafaminol); 7-(1,3-Dioxolan 2-ylmethyl)-theophylline (Doxofylline); 7-(2-Hydroxyethyl)-1,3-dimethylxanthine (Etofylline); 7-(2-Hydroxypropyl)-1,3-dimethylxanthine (Proxyphylline); Pyridoxine-O-(theophyllin-7-ylethyl) sulphate (Pyridofylline); 7-(2-(3-diethylcarbamoylpropionyloxy)ethyl)-theophylline (Suxamidofylline); Piperazine bis(theophyllin-7-ylacetate) (Acepifylline); 8-benzyl-7-(2-(N-ethyl-N-2-hydroxyethylamino)ethyl)theophylline (Bamifylline); 2-amino-2-methylpropan-1-ol theophyllinate (Bufylline)-; 7-(2,3-Dihydroxypropyl)-1,3-dimethylxanthine (Diprophylline); 7-(2-diethylamoinoethyl)-1,3-dimethylxanthine camphor 10 sulphonate (Etamiphylline Camsylate); 3-Propylxanthine (Enprofylline); 4-amino-8-chloro-1-phenyl-(1,2,4)-triazolo (4,3-a)quinoxaline (CP 66713); cysteine/cystine; glycine, forskoline; alpha-2-adrenergic agonist such as brimonidine (UK-14,304), clonidine, apraclonidine, dapiprazole, moxonidine (4-chloro-N-(4,5 dihydro-1H-imidasol-2yl)-6-methoxy-2-methyl-5-pyridinamine), medetomidine, oxymetazoline, or derivatives thereof; peptides such as bradykinin, arginine vasopressin including V2 agonists, bombesine, substance P, pituitary adenylate cyclase activating polypeptide; somatostatin analogues such as Tyr11-somatostatin-14, Leu8, D-Trp22, and Tyr25-somatostatin-28 including agonists of somatostatin sst2 receptors, neuropeptide Y including agonists of Y2 receptors, and anlogues of these peptides; calcitriol or analogues of calcitriol or Vitamin D; muscarine receptor agonists such as the Carbachol, acetylincholine or analogues thereof; nonsteroidal antiinflammatory drugs such as niflumic acid; prostaglandine and analogues thereof such as F2 alpha analogues including PhXA41 (latanoprost), prostaglandin receptor agonists including PGF 2 alpha, 17-phenyl trinor PGE2, and U46619 FP, EP1, and TP receptor agonists), UF 021, 16-phenoxy-PGF2 alpha, cloprostenol, 17-phenyl-PGF2 alpha, fluprostenol, and PhXA85; Thapsigargin, A23187, Phosphodiesterase inhibitors including rolipram and Zaprinast, 4-chloro-3-ethylphenol and Bastidin, veratridine, esterogens including analogues thereof; Bay K 8644 (1,4-Dihydro-2,6-dimethyl-5-nitor-4-(2(triflouromethyl)-phenyl)-3-pyridinencarboxylic acid methyl ester; angiotensin converting enzyme inhibitors, in particular captopril (SQ 14225); adenosine A2-receptor agonists such as 5'(N-ethyl)-carboxamido adenosine and 8-phenylaminoadenosine (CV-1808); Candoxatril (neutral endopeptidase 24.11 (NEP) inhibitor); Met-enkephalin, alphaendorphin or derivatives; and mixtures thereof.

L-cystine is a sulphurous amino acid which is a component of proteins, e.g. collagen, where the above sulphurous crosslinks derive from it. The L-cystine ii thus contained in ordinary food.

In a preferred embodiment, the method comprises use of a mixture of two or more substances having an additive effect on the myopia. In a preferred embodiment, the mixture has a synergistic effect. Both the additive effect and the synergistic effect may by measured by means of the methods described herein, such as by ERG.

In a still further embodiment, the present invention relates to methods for treating and/or preventing hypermetropia of a human eye comprising treatment by means of therapeutically effective amounts of one or more substances selected from theophylline, xanthine, 1,9-dimethylxanthine; 1,3-Dipropyl-8-(2-(5,6-epoxynorbonyl)-xanthine; 8-Cyclopentyl-1,3-dipropylxanthine (CPDPX); 8-Sulphophenyltheophylline; 1,3-Dipropyl-8-(4-acrylate) phenylxanthine (BW-A1433); (1-Propyl-11C)8-dicyclopropylmethyl-1,3-dipropylxanthine (11C)KF15372 and 11C-ethyl and 11C-methyl derivatives thereof; 8-Benzyl-7, (2-(ethyl(2-hydroxyethyl)amino)ethyl) theophylline (Bamiphylline); 8-Cyclopentyl-3-(3-((4-(flourosulfonyl)benzoyl)oxyl)pro-pyl)-1-propylxanthine; 1,3-Dipropyl-8-(4-((2-aminoethyl)amino)carbonylmethyloxyphenyl)xanthine; 6-(3-chlorostyryl)caffeine; 8-cyclopentyltheophylline; 8-(noradamantan-3 yl)-1,3-dipropylxanthine (KW-3902); 1,3-Dipropyl-8-(3-noradamantyl)-xanthine; 1,3-Dipropyl-8-(4-sulphophenyl)-xanthine; 1,3-Dipropyl-8-(2-amino-4-chlorophenyl)-xanthine; 7β-Hydroxyethyl-1,3-dimethylxanthine; 7-(2,3-Dihydroxypropyl)-1,3-dimethylxanthine; 8-Chloro-1,3-dimethylxanthine; 1,3,9-Trimethylxanthine; 8-Propionic acid-1,3-dimethylxanthine; 7,9-Dimethylxanthine; 8-Phenyl-1,3-dimethylxanthine; 7-Acetic acid-1,3-dimethylxanthine; 9-Propylxanthine; 9-Methylxanthine; 8-Methylxanthine; 8-(p-Sulfophenyl)-1,3-dimethylxanthine; 1,9-Dimethylxanthine; hypoxanthine; fluoxetine; L-ornithine; azetazolamide; bumetanide; Tamoxifen and other estrogen antagonists, the calmodulin antagonist J8, calcium antagonists including nimodipine and nicardipine, Endothelin agonist, in particular sarafotoxin S6c (selective ETB receptor agonist); Dorzolamide (MK-507), sezolamide and MK-927 (thienothiopyran-2-sulfonamide derivatives carbonic anhydrase inhibitors), methazolamide, ethoxzolamide, leuenkephalin or dervatives; and mixtures thereof.

In a preferred embodiment, the method comprises use of a mixture of two or more substances having an additive effect on the hypermetropia. In a still more preferred embodiment, the mixture has a synergistic effect. Both the additive effect and the synergistic effect may by measured by means of the methods described herein, such as by ERG.

Use of a mixture may also be preferred when minor total dosages of each of the substances are preferred compared to a higher total dosage of only one substance.

The active substance or mixture of substances according to the invention may be administered orally, parenterally, transdermally or transmucosally e.g. as an intranasal formulation or as eyedrops. In addition, a local application in the eye may result in a substantial local concentration of the substance in the retinal area due to the anatomical circumstances of the eye whereby a less systemic effect is achieved. This is e.g. the fact where the substance is applied topically to the eye and where the drainage of the substance is by the uveoscleral pathway.

The pharmaceutical composition according to the invention comprising the active substance or mixture of substances may be administered in the form of a pharmaceutical composition which is a tablet, a capsule, a sustained release capsule comprising micro capsules of the active ingredient, a solution or suspension, a device for transdermal application, or a suppository or implant, or in any other conventional formulation.

As the treatment or prevention of abnormal growth of the eye is a longterm treatment to children, the active substance or mixture of substances may be incorporated into a general daily vitamin tablet or be incorporated into foodstuff, socalled functional foods, including softdrinks, milk, bread, etc.

It is also an aspect of the present invention, that the individual substances may be interchanged during a treatment period, or that one substance is administered in an individual dosage, e.g in the morning, and another substance is administered in the evening.

In a further aspect of the invention the active ingredient is derived from the biological natural sources. Several methylxanthines naturally occurs in plants. More than 60 plant species throughout the world have been identified as containing 1,3,7-trimethylxanthine, 1,7-dimethylxanthine, 1,3-dimethylxanthine, 1-methylxanthine, 3-methylxanthine, or 7-methylxanthine. These plants includes the species coffea, camellia, cola, paullinia (guarana), iles (maté), theobroma, citrus, geraniaceae, copermecia, phaseolul, mungo, soya bean, beta vulgaris, sugar cane, and xanthophycae. Since the active substances often represents different steps in the synthesis or degradation of more complex methylxanthines, several xanthines may be present in the same plant in concentrations that variate with the season of the year.

Harvesting the plant at different periods of the season, and using different extraction methods will result in extracts containing high concentration of certain methylxanthines with only minor contributions of other, and less desired methylxanthines. In a further embodiment of the invention, a extraction method is described that results in a composition rich in 7-methylxanthine, taking advantage of the fact that 7-methylxanthines is more easily dissolved than the other methylxanthines.

Other embodiments relates to extraction of beta vulgaris, sugar canes, xanthophycae and other plants comprising 7-methylxanthines.

Depending on the exact dissolving properties of the desired active ingredient, the extraction method may be adapted for the specific plant as well as for the desired active ingredient.

Examples of a suitable extraction method is given below in Examples 6 and 7.

In a still other aspect, the active ingredient for treating or preventing disease of the longitudinal growth of the eye may be produced by genetic engineering such as by transgenic plants expressing the active ingredient or by other biotechnological methods.

In addition to genetic manipulation, the plant material, for the purpose of increasing the yield of certain methylxanthines from the plant material, the plant may be subjected to treatment with substances that block or facilitate certain enzymes that determines the metabolism of the metylxanthines. As an example of this, treatment of coffee plants with allopurinol will result in accumulation of great amounts of 7-methylxanthine in the plant (Ashihara H (1996). Catabolism of caffeine and related purine alkaloids i leaves of coffea arabica; L. Planta 1998:334–339)

Registration of c-Wave at ERG in animals (e.g. rabbits) is a well-developed examination technique (Skoog, K. O., Nilsson, S. E. G., Acta Ophthalmol. (Kph), 52: 759–773 (1974), Jarkman, S., Skoog, K. O., Doc. Ophthalmol., 60: 383–392 (1985)). Also intraoccular administration of test substances for test animals is also a well-described-technique (Textorius O., Doc. Ophthalmol., 63:349–358 (1986)). Alternatively, test substances can be administered intravenously (Jarkman, S., Doc. Ophthalmol. 60: 375–382 (1985)).

In addition, it is possible to determine the effect of test substances on the standing potential and c-wave at ERG indirectly by means of an in vitro arrangement with a retinal pigment epithelium-choroidea preparation, and to determine the transepithelial potential (Kawasaki, K., Doc. Ophthalmol., 63: 375–381 (1986)).

By means of such examination techniques which can facilitate quick examinations it is according to the present invention possible to examine a large number of substances in various concentrations and to determine which substances have a strong effect on the activity of the pigment epithelium of the retina.

Determination of the content of proteoglycanes in tissue samples can be performed by means of several well-developed methods (eg. Björnsson, S., Analytical Biochemistry 210, 282–291 (1993)).

The content of the collagen specific amino acids (hydroxyproline, hydroxylysine, and proline) can be determined eg. by means of autoanalysis (Blumenkrantz, N., Clin. Biochem. 13: 177–183 (1980)) or by means of high pressure liquid chromatography (HPLC) or other methods. A method for determination of the content of collagen specific amino acids in connective tissue by means of application of HPLC has been described in detail below.

A method for determination of the content of dermatane sulphate in percentages in relation to the other glycosaminoglycanes (cellulose acetate electroforese) has been described in detail below.

The following Table 1 shows a number of specific preferred xanthine substances according to the present invention effective for treating and/or preventing myopia, and in Table 2 for hypermetropia.

TABLE 1

Substances effective for treating and/or preventing myopia 1. 1,3-Bis(3-methylbut-2-butenyl-7-methylxanthine
2. 3,7-Dihydro-7-methyl-1,3-dipropyl-1H-purine-2,6-dione
3. 7-Methyl-1,3-diprenylxanthine(7-methyl-1,3-dipropyl-xanthine[1]
4. 7-Ethoxymethyl-1-(5-hydroxy-5-methylhexyl)3-methylxanthine (Torbafylline, "HWA 448")
5. 1-(5 hydoxy-5-methylhexyl)-3-methyl-7-propylxanthine (A 80.2715)
6. 3,7-Dimethyl-1-(5-oxyhexyl)-xanthine (Pentoxifylline, "Trental")
7. 3,7-Dimethyl-1-(5-hydroxyhexyl)-xanthine (Hydroxypentoxifylline)
8. 1-Hexyl-3,7-dimethylxanthine (Pentifylline, "Cosaldon")
9. 3,7-Dimethyl-1-proparglyxanthine (DMPX)[2]
10. (E)-8-(3,4-Dimethoxystyryl)-1,3-dipropyl-7-methylxanthine (KF 17837) (Lisofylline)
11. 1-(5-Hydroxy-5-methylhexyl)-3-methylxanthine (Albifylline, "HWA 138")
12. 3-Methyl-1-(5'-oxohexyl)-7-propylxanthine (Propentofylline, "HWA 285")
13. 1-(5-Hydroxyhexyl)-3,7-dimethylxanthine (BL 194)
14. (E)-1,3-dipropyl-8-(3,4-dimethoxystyryl)-7-methylxanthine (KF 17.837)[1]
15. 1,3-di-n-butyl-7-(2'oxopropyl)-xanthine (Denbufylline)
16. 1-n-butyl-3-n-propylxanthine (XT-044)
17. 7-(2,3-dihydroxypropyl)-theophylline (Dyphylline)
18. 7-Methyl-8-(2-hydroxy-N-methylethylamino)-theophylline (Cafaminol)
19. 7-(1,3-Dioxolan 2-ylmethyl)-theophylline (Doxofylline)
20. 7-(2-Hydroxyethyl)-1,3-dimethylxanthine (Etofylline)
21. 7-(2-Hydroxypropyl)-1,3-dimethylxanthine (Proxyphylline)
22. Pyridoxine-O-(theophyllin-7-ylethyl)sulphate (Pyridofylline)
23. 7-(2-(3-diethylcarbamoylpropionyloxy)ethyl)theophylline (Suxamidofylline)
24. Piperazine bis (theophyllin-7-ylacetate) (Acepifylline)
25. 8-benzyl-7-(2-(N-ethyl-N-2-hydroxyethylamino)ethyl)theophylline (Bamifylline)
26. 2-amino-2-methylpropan-1-ol theophyllinate (Bufylline)
27. 7-(2,3-Dihydroxypropyl)-1,3-dimethylxanthine (Diprophylline)
28. 7-(2-diethylamoinoethyl)-1,3-dimethylxanthine camphor 10 sulphonate (Etamiphylline Camsylate)
29. 3-Propylxanthine (Enprofylline)
30. 4-amino-8-chloro-1-phenyl-(1,2,4)-triazolo (4,3-a)quinoxaline (CP 71366)[1]

TABLE 2

Substances effective for treating and preventing of hypermetropia 31. 1,3-Dipropyl-8-(2-(5,6-epoxynorbornyl)-xanthine[3]
32. 8-Cyclopentyl-1,3-dipropylxanthine (CPDPX)[4]
33. 8-Sulphophenyltheophylline
34. 1,3-Dipropyl-8-(4-acrylate)phenylxanthine (BW-A1433)[5]

TABLE 2-continued

Substances effective for treating and preventing of hypermetropia 35. (1-Propyl-11C)8-dicyclopropylmethyl-1,3-dipropylxanthine (11C)KF15372
    and 11C-ethyl and 11C-methyl derivatives thereof All[4]
36. 8-Benzyl-7,(2-(ethyl(2-hydroxyethyl)amino)ethyl)theophylline (Bamiphylline)
37. 8-Cyclopentyl-3-(3-((4-(flourosulfonyl)benzoyl)oxy)propyl)-1-propylxanthine[3]
38. 1,3-Dipropyl-8-(4-((2-aminoethyl)amino)carbonylmethyloxyphenyl)xanthine
39. 8-(3-chlorostyryl)caffeine
40. 8-cyclopentyltheophylline[3]
41. 8-(noradamantan-3 yl)-1,3-dipropylxanthine (KW-3902)
42. 1,3-Dipropyl-8-(3-noradamantyl)-xanthine[3]
43. 1,3-Dipropyl-8-(4-sulphophenyl)-xanthine
44. 1,3-Dipropyl-8-(2-amino-4-chlorophenyl)-xanthine
45. Hypoxanthine

[1]A2 antagonist
[2]Selective A2 antagonist
[3]A1 antagonist
[4]Selective A1 antagonist
[5]A3 receptor antagonist

TABLE 3

Effect of xanthines on [$^3$H]ryanodine binding to skeletal RyR

| | Bound [$^3$H]ryanodine, % of control | +3 mmol/l AMP | +1 mmol/l AMPPCP |
|---|---|---|---|
| Control (-xanthine) | 100 | 100 | 100 |
| 1-Hexyl-3,7-dimethyl-xanthine (pentifylline) | 549 ± 33* | 449 ± 28* | 414 ± 47* |
| 1,7-Dimethyl-xanthine | 240 ± 27* | 378 ± 34* | 360 ± 28* |
| 1,3-Dipropyl-7-methyl-xanthine | 220 ± 23* | 326 ± 30* | 295 ± 23* |
| 7-Propylxanthine | 216 ± 25* | 234 ± 14* | 270 ± 12* |
| 7β-Chloroethyl-1,3-dimethylxanthine | 220 ± 27* | 256 ± 34* | 230 ± 9* |
| 3,7-Dimethyl-1-propargylxanthine | 193 ± 15* | 201 ± 33* | 230 ± 6* |
| 3-Propylxanthine | 211 ± 13* | 203 ± 14* | 226 ± 14* |
| 7-Methylxanthine | 204 ± 25* | 214 ± 15* | 225 ± 11* |
| 1-(5-Oxohexyl)-3,7-dimethylxanthine (pentoxyfylline) | 187 ± 16* | 185 ± 25* | 188 ± 5* |
| 1,3,7-Trimethylxanthine (caffeine) | 155 ± 22* | 164 ± 11* | 182 ± 18* |
| 1-Methylxanthine | 153 ± 15* | 167 ± 16* | 179 ± 22* |
| 3-Isobutyl-1-methyl-xanthine | 137 ± 16* | 139 ± 11* | 175 ± 20* |
| 1,3-Dimethylxanthine (theophylline) | 136 ± 29* | 148 ± 8* | 170 ± 25* |
| 3,7-Dimethylxanthine (theobromine) | 124 ± 22* | 136 ± 8* | 160 ± 22* |
| 3,9-Dimethyl-xanthine | 146 ± 26* | 141 ± 11* | 143 ± 20* |
| 3-Methylxanthine | 155 ± 24* | 137 ± 10* | 134 ± 9* |
| 8-Cyclopentyl-1,3-dimethylxanthine | 155 ± 24* | 142 ± 14* | 133 ± 6* |
| 7β-Hydroxyethyl-1,3-dimethylxanthine | 113 ± 13* | 134 ± 15* | 124 ± 15* |
| 7-(2,3-Dihydroxypropyl)-1,3-dimethylxanthine | 100 ± 16 | 123 ± 16* | 117 ± 9* |
| 8-Chloro-1,3-dimethyl-xanthine | 98 ± 25 | 108 ± 14 | 116 ± 17 |
| 1,3,9-Trimethyl-xanthine | 103 ± 18 | 103 ± 15 | 105 ± 7 |
| 8-Propionic acid 1,3-dimethylxanthine | 113 ± 13 | 100 ± 11 | 102 ± 5 |
| 7,9-Dimethyl-xanthine | 99 ± 14 | 100 ± 15 | 102 ± 13 |

TABLE 3-continued

Effect of xanthines on [³H]ryanodine binding to skeletal RyR

| | Bound [³H]ryanodine, % of control | +3 mmol/l AMP | +1 mmol/l AMPPCP |
|---|---|---|---|
| 8-Phenyl-1,3-dimethyl-xanthine | 109 ± 11 | 103 ± 14 | 99 ± 18 |
| 7-Acetic acid-1,3-dimethylxanthine | 93 ± 15 | 99 ± 12 | 98 ± 19 |
| 9-Propylxanthine | 102 ± 24 | 97 ± 23 | 96 ± 12 |
| 9-Methylxanthine | 96 ± 11 | 85 ± 18 | 98 ± 10 |
| 8-Methylxanthine | 109 ± 9 | 90 ± 11 | 95 ± 20 |
| 8-(p-Sulfophenyl)-1,3-dimethylxanthine | 95 ± 7 | 91 ± 16 | 92 ± 17 |
| 1,9-Dimethyl-xanthine | 76 ± 13 | 86 ± 18 | 84 ± 14 |

(Specific [³H] ryanodine binding was determined as described in Materials and Methods in Liu et AL., Structure-activity Relationship of Xanthines and Skeletal Muscle Ryanodine Receptor/Ca²⁺ Release Channel; Pharmacology 1997;54:135–143. Xanthine concentrations were 1.5 mmol/l. Control [³H] ryanodine binding values (-xanthines) were 0.55±0.05, 0.73±0.08 and 1.69±0.12 pmol/mg protein in the absence and presence of 3 mmol/l AMP or 1 mmol/l AMPPCP, respectively. * Significantly different from control at p<0.05.)

From the above Table 3 it is seen that nonpolar residues in positions, 1, 3 and 7 stimulated [³H] ryanodine binding, whereas nonpolar residues in positions 8 and 9 counteracted the effect.

According to the present invention, substances which have an effect on the [³H] ryanodine binding of at least 130%, preferable more than 150% of that of the control xanthine are effective for treating or preventing disease related to excessive longitudinal growth of the eye, and substances, which have an effect on the [³H] ryanodine binding of less than 130%, preferable less than 100% of that of the control xanthine are effective for treating or preventing disease of insufficient longitudinal growth of the eye.

According to the present invention, the substances disclosed in Table 3 having the highest binding effect are most preferred for treating of myopia, such as the substance showing an effect on the [³H] ryanodine binding of more than 200% compared to the control xanthine, and includes the substance Pentifylline. The substances disclosed in Table 3 having the lowest binding effect are most preferred for treating of hypermetropia, such as the substance showing an effect on the [³H] ryanodine binding of less than 110% compared to the control xanthine, and includes the substance 1,9-dimethylxanthine.

TABLE 4

Effect of xanthines on [³H]ryanodine binding to skeletal RyR in the presence of 1 mmol/l AMPPCP

| | Bound [³H]ryanodine | |
|---|---|---|
| | pmol/mg protein | % of control |
| Monosubstituted xanthines | | |
| Control (-xanthine) | 1.69 ± 0.12 | 100 |
| 7-Propyl- | 4.57 ± 0.20 | 270 ± 12* |
| 3-Propyl- | 3.82 ± 0.23 | 226 ± 14* |
| 7-Methyl- | 3.80 ± 0.19 | 225 ± 11* |
| 1-Methyl- | 3.02 ± 0.38 | 179 ± 22* |

TABLE 4-continued

Effect of xanthines on [³H]ryanodine binding to skeletal RyR in the presence of 1 mmol/l AMPPCP

| | Bound [³H]ryanodine | |
|---|---|---|
| | pmol/mg protein | % of control |
| 3-Methyl- | 2.26 ± 0.15 | 134 ± 9* |
| 9-Propyl- | 1.62 ± 0.20 | 96 ± 12 |
| 9-Methyl- | 1.66 ± 0.17 | 98 ± 10 |
| 8-Methyl- | 1.61 ± 0.33 | 95 ± 20 |
| Disubstituted xanthines | | |
| Control (-xanthine) | 1.69 ± 0.12 | 100 |
| 1,7-Dimethyl- | 6.08 ± 0.47 | 360 ± 28* |
| 3-Butyl-1-methylxanthine | 2.96 ± 0.33 | 175 ± 20* |
| 1,3-Dimethyl-(theophylline) | 2.87 ± 0.42 | 170 ± 25* |
| 3,7-Dimethyl-(theobromine) | 2.70 ± 0.37 | 160 ± 22* |
| 3,9-Dimethyl- | 2.42 ± 0.34 | 143 ± 20* |
| 7,9-Dimethyl- | 1.73 ± 0.22 | 102 ± 13 |
| 1,9-Dimethyl- | 1.42 ± 0.23 | 84 ± 14 |
| 1-Substituted 3,7-dimethylxanthines | | |
| 3,7-Dimethyl-xanthine(control) | 2.70 ± 0.37 | 100 |
| 1-Hexyl-(pentifylline) | 6.99 ± 0.80 | 259 ± 24* |
| 1-Propargyl- | 3.88 ± 0.10 | 144 ± 3* |
| 1-(5-Oxohexyl)-(pentoxyfylline) | 3.18 ± 0.08 | 118 ± 3* |
| 1-Methyl-(caffeine) | 3.07 ± 0.30 | 114 ± 2 |
| 7-Substituted 1,3-dimethylxanthines | | |
| 1,3-Dimethyl-xanthine(control) | 2.87 ± 0.42 | 100 |
| 7β-Chloroethyl- | 3.88 ± 0.16 | 135 ± 6* |
| 7-Methyl-(caffeine) | 3.07 ± 0.301 | 107 ± 4 |
| 7β-Hydroxyethyl- | 2.10 ± 0.26 | 73 ± 4* |
| 7-(2,3-Dihydroxypropyl)- | 1.97 ± 0.16 | 69 ± 6* |
| 7-Acetic acid- | 1.65 ± 0.32 | 57 ± 6* |
| 8-Substituted 1,3-dimethylxanthines | | |
| 1,3 Dimethyl-xanthine(control) | 2.87 ± 0.42 | 100 |
| 8-Cyclopentyl- | 2.25 ± 0.28 | 78 ± 8 |
| 8-Chloro- | 1.96 ± 0.13 | 68 ± 4* |
| 8-Propionic acid- | 1.73 ± 0.09 | 60 ± 3* |
| 8-Phenyl- | 1.67 ± 0.31 | 58 ± 9* |
| 8-(p-Sulfophenyl)- | 1.55 ± 0.28 | 54 ± 6* |
| Others | | |
| 1,3-Dipropyl-7-methyl-xanthine | 4.96 ± 0.39 | |
| 1,3,9-Trimethylxanthine | 1.77 ± 0.12 | |

([³H] ryanodine-binding measurements were determined as described in Materials and Methods in Liu et AL., Structure-activity Relationship of Xanthines and Skeletal Muscle Ryanodine Receptor/Ca²⁺ Release Channel; Pharmacology, 1997;54:135–143. Xanthine concentrations were 1.5 mmol/l. The control bound [³H] ryanodine for each subgroup was set equal to 100. Results are means±SD of 3–4 separate experiments. * Significantly different from controls at p<0.05.)

From this Table 4, the effect of the individual substituents to the xanthine molecule structure is clearly demonstrated.

Xanthines which is substituted in one or more of position 1, 3, and 7 (of the general formula of xanthine shown i FIG. 3) with any of the following substituents: hydroxy, halogen, triflourmethyl, lower alkyl ($C_{1-6}$), tertiary amino/alkoxy are preferred for the treatment or prevention of myopia.

On the other hand, when the xanthine is substituted in one or more of position 8 and 9 with these substituents, the substance is useful for treatment or prevention of hypermetropia, especially if the xanthine is only substituted in these positions.

When the xanthine is substituted in both positions 7 and 9, such as in 7,9-Dimethylxanthine, the double bond between the nitrogen atom and carbon atom as shown in the general formula (I) is hydrogenated as appears from formula III.

In the present context, the term "$C_{1-20}$-alkyl" is intended to mean a linear, cyclic or branched hydrocarbon group having 1 to 20 carbon atoms, such as methyl, ethyl, propyl, iso-propyl, cyclopropyl, butyl, tert-butyl, iso-butyl, cyclobutyl, pentyl, cyclopentyl, hexyl, cyclohexyl, hexadecyl, heptadecyl, octadecyl, nonadecyl. Analogously, the term "$C_{1-6}$-alkyl" is intended to mean a linear, cyclic or branched hydrocarbon group having 1 to 6 carbon atoms, such as methyl ethyl, propyl, iso-propyl, pentyl, cyclopentyl, hexyl, cyclohexyl.

Preferred examples of "$C_{1-6}$-alkyl" are methyl, ethyl, propyl, iso-propyl, butyl, tert-butyl, iso-butyl, pentyl, cyclopentyl, hexyl, cyclohexyl, in particular methyl, ethyl, propyl, iso-propyl, tert-butyl, iso-butyl and cyclohexyl.

Similarly, the terms "$C_{2-20}$-alkenyl", "$C_{4-20}$-alkadienyl", and "$C_{6-20}$-alkatrienyl" are intended to mean a linear, cyclic or branched hydrocarbon group having 2 to 20, 4 to 20, and 6 to 20, carbon atoms, respectively, and comprising one, two, and three unsaturated bonds, respectively. Analogously, the term a "$C_{2-6}$-alkenyl" is intended to mean a linear, cyclic or branched hydrocarbon groups having 2 to 6 carbon atoms and comprising one double bond.

Examples of alkenyl groups are vinyl, allyl, butenyl, pentenyl, hexenyl, heptenyl, octenyl, heptadecaenyl. Examples of alkadienyl groups are butadienyl, pentadienyl, hexadienyl, heptadienyl, heptadecadienyl. Examples of alkatrienyligroups are hexatrienyl, heptatrienyl, octatrienyl, and heptadecatrienyl.

The term "$C_{2-20}$-alkynyl" is intended to mean a linear or branched hydrocarbon group having 2 to 20 carbon atoms and comprising a triple bond. Examples hereof are ethynyl, propynyl, butynyl, octynyl, and dodecaynyl. Analogously, the term "$C_{2-6}$-alkynyl" is intended to mean a linear or branched hydrocarbon groups having 2 to 6 carbon atoms and comprising one triple bond, such as ethynyl, propynyl, butynyl, pentynyl, and hexynyl.

In the present context the term "alkoxy" means alkyl-oxy, and "halogen" means fluoro, chloro, bromo, iodo.

In the present context, i.e. in connection with the terms "alkyl", "alkenyl", "alkadienyl", "alkatrienyl", "alkynyl", and "alkoxy", the term "optionally substituted" is intended to mean that the group in question may be substituted one or several times, preferably 1–3 times, with group(s) selected from hydroxy (which when bound to an unsaturated carbon atom may be present in the tautomeric keto form), $C_{1-6}$-alkoxy (i.e. alkyl-oxy), $C_{2-6}$-alkenyloxy, carboxy, oxo (forming a keto or aldehyde functionality), $C_{1-6}$-alkoxycarbonyl, $C_{1-6}$-alkylcarbonyl, formyl, aryl, aryloxycarbonyl, aryloxy, arylcarbonyl, heteroaryl, heteroaryloxycarbonyl, heteroaryloxy, heteroarylcarbonyl, amino, mono- and di($C_{1-6}$-alkyl)amino; carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkylaminocarbonyl, $C_{1-6}$-alkylcarbonylamino, guanidino, carbamido, $C_{1-6}$-alkanoyloxy, sulphono, $C_{1-6}$-alkylsulphonyloxy, nitro, sulphanyl, $C_{1-6}$-alkylthio, trihalogen-$C_{1-6}$-alkyl, halogen such as fluoro, chloro, bromo or iodo, where aryl and heteroaryl may be substituted as specifically described below for "optionally substituted aryl and heteroaryl".

In the present context the term "aryl" is intended to mean a fully or partially aromatic carbocyclic ring or ring system, such as phenyl, naphthyl, 1,2,3,4-tetrahydronaphthyl, anthracyl, phenanthracyl, pyrenyl, benzopyrenyl, fluorenyl and xanthenyl, among which phenyl is a preferred example.

The term "heteroaryl" is intended to mean a fully or partially aromatic carbocyclic ring or ring system where one or more of the carbon atoms have been replaced with heteroatoms, e.g. nitrogen, sulphur, and/or oxygen atoms. Examples of such heteroaryl groups are oxazolyl, isoxazolyl, thiazolyl, isothiazolyl, pyrrolyl, imidazolyl, pyrazolyl, pyridinyl, pyrazinyl, pyridazinyl, piperidinyl, coumaryl, furyl, quinolyl, benzothiazolyl, benzotriazolyl, benzodiazolyl, benzooxozolyl, phthalazinyl, phthalanyl, triazolyl, tetrazolyl, isquinolyl, acridinyl, carbazolyl, dibenzazepinyl, indolyl, benzopyrazolyl, phenoxazonyl. Preferred heteroary groups are pyridinyl, benzopyrazolyl, and imidazolyl.

In the present context, i.e. in connection with the terms "aryl" and "heteroaryl", the term "optionally substituted" is intended to mean that the group in question may be substituted one or several times, preferably 1–5 times, in particular 1–3 times) with group(s) selected from hydroxy (which when present in an enol system may be represented in the tautomeric keto form), $C_{1-6}$-alkyl, $C_{1-6}$-alkoxy, oxo (which may be represented in the tautomeric enol form), carboxy, $C_{1-6}$-alkoxycarbonyl, $C_{1-6}$-alkylcarbonyl, formyl, aryl, aryloxy, aryloxycarbonyl, arylcarbonyl, heteroaryl, amino, mono- and di($C_{1-6}$-alkyl)amino; carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, guanidino, carbamido, $C_{1-6}$-alkanoyloxy, sulphono, $C_{3-6}$-alkyl-sulphonyloxy, nitro, sulphanyl, dihalogen-$C_{1-4}$-alkyl, trihalogen-$C_{1-4}$-alkyl, halogen such as fluoro, chloro, bromo or iodo, where aryl and heteroaryl representing substituents may be. Preferred examples are hydroxy, $C_{1-6}$-alkyl, $C_{1-6}$-alkoxy, carboxy, $C_{1-6}$-alkoxycarbonyl, $C_{1-6}$-alkylcarbonyl, aryl, amino, mono- and di($C_{1-6}$-alkyl)amino, and halogen such as fluoro, chloro, bromo or iodo, wherein aryl and heteroaryl may be substituted as above.

The pharmaceutical preparation according to the present invention may be formulated in accordance with conventional pharmaceutical practice with pharmaceutical excipients conventionally used for the preparation of oral, topical and systemical formulations. In addition, many of the substances are well known medical formulations.

The concentration of the substance or mixture of substances may be present in the medicament in an amount of 0.001–99%, typically 0.01–75%, more typically 0.1–20%, especially 1–10% by weight of the medicament, however, for many of the substances are already avaible for pharmaceutical use, and generally, the substances are then to be used in ordinary clinical dosages and concentrations known in the litterature.

In another aspect of the invention, the dosage is correlated to an effect similar to the effect of the testes drugs of the present invention and which appears from the examples. This correlation may be performed by the measuring methods as described en the present text.

The preparation of the invention may also contain other additives such as emulsifieres, stabilizing agents, preservatives, etc.

The invention is furthermore described in the claims and rendered probable in the following examples.

List of Examples

Example 1 Materials and Methods
Example 2 Biochemical changes in rabbit sclera after long term treatment with Fluoxetine, Teofylamin; Caffeine and L-cysteine.
Example 3 Effect of myopia progression in a human by treatment with caffeine and L-cysteine.
Example 4 Biochemical changes in rabbit sclera after long-term treatment with 7-methylxanthine, Theobromine, Acetazolamide, and L-ornithine.
Example 5 Effect on proteoglycanes compared with effect on [$^3$H] ryanodine binding of different xanthines.
Example 6 Extraction method for substance from natural source.
Example 7 Extraction method for substance from natural source.
Example 8 Experiments under investigation:

Comments to the Examples

On the basis of the biochemical results in Example 2 it is likely that a treatment of myopia with caffeine will be more efficient than L-cystine as a moderate dosage of caffeine unambiguously affects all parameters appropriately.

In humans caffeine has a realtively long half-life period (approximately 5 hours). After administration of a dosage of caffeine, the serum concentration of caffeine is therefore dominant, however, with an essential contribution of the pharmacologically active metabolites 1,7-dimethylxanthine (paraxanthine), 3,7-dimethylxanthine (theobromine), and 1,3-dimethylxanthine (theophylline), 1-methylxanthine, 3-methylxanthine, and 7-methylxanthine (heteroxanthine).

In rabbits the half-life period for caffeine is short (approximately 1 hour) and the most essential contribution for the serum concentration comes from the metabolite 1,7-dimethylxanthine whereas the serum concentration of caffeine will be essentially lower.

The strong effect of caffeine on the biochemical composition of sclera, as it appears from Example 2, is believed to be due to the above-mentioned metabolites of caffeine.

Example 3 demonstrates that substances identified according to Example 2 of having specific effects on the biochemical composition of sclera of a non-human mammal, the rabbit, in fact are able to prevent inappropriate growth of the eye in a human.

Example 4 shows that the caffeine metabolite theophylline (1,3-dimethylxanthine) partly reduces c-wave at ERG and the standing potential of the eye, and partly reduces the content of proteoglycanes in sclera. Theophylline does increase the content of the collagen specific amino acids hydroxyproline and proline, but it reduces the content of hydroxylysine. In total theophylline therefore has an inhibiting effect on the content of connective tissue components and thus a directly opposite effect as compared to the closely familiar substance caffeine.

Caffeine is transformed after administration partly to theophylline which works against the stimulating effect of caffeine on the scleral tissue. In order to avoid this weakening effect those metabolites can be employed for caffeine which is not transformed into theophylline.

Theophylline only differs from caffeine by not having a 7-methyl group. Other appropriate substances for treatment of myopia among caffeine derivatives or analogues with a 7-methyl group include. 1,7-dimethylxanthine (paraxanthine), and 7-methylxanthine (heteroxanthine) are especially interesting, however also 3-methylxanthine and 1-methylxanthine are believed to be effective against myopia.

Other 7-methyl xanthines which can be effective for treatment of myopia can involve derivatives of xanthine having substituents in other positions than the 7-position. In a similar way, xanthines derivatives not having a methyl group in the 7-position may be useful for the treatment of hypermetropia.

EXAMPLE 1

Materials and Methods

Test animal: Charles River Deutschland Chinchilla Bastard female rabbits.
Number of animals: 6 test animals and 6 control animals
Age: approximately 8 weeks at the commencement of the test.
Weight: 1.4–1.9 kg at the commencement of the test.
Lightness/Darkness cycle: 12/12 hours.
Water: ad libitum.
Cages: The animals live in identical cages made of stainless steel (Scanbur), length 1 m, depth 0.52 m, height 0.5 m.
Food: Stanrab standard diet from Special Diet Services, P.O. Box 705, Witham Essex CM8 3AD, UK (further details, see Table A).
Amount of food: Increasing from 75 g per day at the commencement of the test up to 130 g after three months.

Experimental drinking water 1 contained theophyllin in a dose equivalent of 27 mg increasing to 63 mg (added as theophyllin and ethylendiamin in a dose of 33 to 77 mg) daily.

Experimental drinking water 2 contained fluoxetine (Fontex, Lilly) in a dose equivalent of 2 mg increasing to 5 mg daily.

Experimental diet 1 was added caffeine (1,3,7-trimethylxanthine) 500 mg per kg Stanrab standard diet equivalent of a daily caffeine dose of 37.5 g increasing to 65 g per day.

Experimental diet 2 was added 4.5 g L-cystine per kg Stanrab standard diet equivalent of a daily L-cystine dose of 338 mg increasing to 585 mg per day. With respect to the supplement of L-cystine, the normal intake per day of the standard diet is 218 mg increasing to 377 mg L-cystine.

Experimental diet 3 was added 7-methylxanthine 500 mg per kg Stanrab standard diet equivalent of a daily 7-methylxanthine dose of 37.5 g increasing to 65 g per day.

Experimental diet 4 was added theobromine (3,7-dimethylxanthine) 500 mg per kg Stanrab standard diet equivalent of a daily theobromine dose of 37.5 g increasing to 65 per day.

Experimental diet 5 was added acetazolamide 500 mg per kg Stanrab standard diet equivalent of a daily acetazolamide dose of 37.5 g increasing to 65 g per day.

Experimental diet 6 was added 4.5 g L-ornithine per kg Stanrab standard diet equivalent of a daily L-ornithine dose of 338 mg increasing to 585 mg per day.

Collection of sample: Sclera biopsies are taken for analysis for proteoglycane content, distribution between the individual glycosaminoglycanes and the content of collagen specific amino acids. Four tests from each animal: Two samples from the front, 5×10 mm along limbus (without cornea), and two samples from the back, punch 10 mm corresponding to the center of the retina. Furthermore, tests are taken for electron microscopy (EM) from two animals in each group.

Analyses: Samples for proteoglycane analysis are frozen down immediately. The samples are analyzed by Wieslab AB, IDEON, S-223 70 Lund, Sweden, by means of a method which has been described by Björnsson, S., Analytical Biochemistry 210, 282–291 (1993). The method comprises extraction by 20 microliters of 4 M guanidine-HCl, 50 Mm sodium acetate per mg wet weight over night by room temperatures. The extracts are centrifuged in order to remove debris. 20 microliters of supernatant are reduced 1/10 in extraction buffer and 20 microliters of reduced supernatant are mixed with 10 microliters of reagent 1 (see Björnsson, S., Analytical biochemistry 210, 282–291 (1993)) on a shaking table for 15 minutes. 200 microliters of reagent 2 are added and the tests are incubated for 60 minutes in order to precipitate the proteoglycanes. The proteoglycane/alcian blue precipitate is transferred to 96-wells MillBlotD apparatus and washed with 2×200 microliters of 40% DMSO, 0.05 M of $MgCl_2$. The colour intensity of the wells are quantitated by microtech E3 scanner and Scan Analysis software (Biosoft, Cambridge, U.K.). Chrondroitine-6-sulphate (Sigma C4384) is used as the calibrator. All samples are analyzed in duplicate.

Samples for analysis for content of collagen specific amino acids are frozen down immediately. The amino acid content is determined by HPLC-chromatography. The tissue bits are delipidized with acetone at 4° C. in 3×24 hours, then with acetone:diethylether 1:1 for 24 hours, and finally 1 hour of standing with pure diethylether.

Then they are dried to constant weight by standing in vacuum exsiccator for 1.5 hours with the pump on and after closure standing over night.

The dried tissue with constant weight is minced into very fine particles with a pair of scissors, approximately 20 per piece of tissue. The small flakes from each original piece of tissue ate divided into two equally sized portions, one of which is employed for hydrolysis and the other one is kept for reference. The constant dry weight of each portion is known.

The finely divided tissue is hydrolyzed in Pyrex glass tubes for 24 hours at 114° C., and subsequently the hydrolysates are dried (removal of remnants from of hydrochloric acid) by standing in vacuum exsiccator at 40° C. over night. The dry residue of hydrolysate is resolubilized in 320 microliter of 0.1 N hydrochloric acid by standing in ultrasound bath for 10 minutes vortexing and then standing over night at 4° C. surrendered by a final wortexing and centrifugation.

From each resolubilized hydrolysate 3 aliquots of each 8 microliters and 3 aliquots of 40 µl are taken and transferred to separate polypropylene tubes in which 20 microliters of a solution of internal standard substances citrulline and 2 aminobutyric acid were added where the further method takes place.

The taken aliquots from hydrolysate are dried in a vacuum exsiccator at 35° C. over night and subsequently submitted to derivatization with phenylisothiocyanate.

The resulting phenylisothiocarbamates are transferred to the HPLC instrument for separation and quantification. A new set of calibration curves is established, 1 curve for each of the 19 amino acids, prior to the analysis of the samples from one investigation.

The concentration range of standard samples exceed the ranges of amino acid concentrations in the unknowns. Hydroxyproline and proline are quantitated from the 8 microliter aliquots, and hydroxylysine is quantitated from the 40 microliter aliquots.

The curves were straight with a high coefficient of correlation.

Samples for analysis of the distribution between the various glycosaminoglycanes are immediately put in acetone. The analysis is made with a method described by Olsen, E. B., Acta Orthop. Scand. 60 (1), 23–25 (1989), comprising delipidization, drying, digestion with pronase. The glycosaminoglycanes are separated in the procedure comprising centyltrimethyl ammonium bromide. The glycosaminoglycane centyltrimethyl ammonium bromide complex is washed with ethanol saturated with NaCl in order to remove centyltrimethyle ammonium bromide. The cleaned Na-glycosaminoglycanes are dried and resolubilized in NaOH and distilled water for further analysis. The individual glycosaminoglycanes are separated by means of cellulose acetate electroforese, and the relative content of the essential glycosaminoglycanes are measured by means of optical scanning.

EM is made on ultra thin cuts from the center part of the biopsies after fixation in 4% of glutaraldehyde in caccodylate buffer with 7.5% sucrose at 4° C. over night, dehydrated in ethanol and moulded in epoxy resin. The cuts are stained with saturated uranyl acetate solution in 50% of ethanol for 1 hour, followed by lead citrate (Reynolds) for 3 minutes for routine electron microscopy.

Ultra thin cuts are collected on gold nets and stained by means of periodine acid-silver proteinate technique for glucoproteins (PAS) and with 0.1% of ruthenium red solution in 0.1 M ammonia for acidic glycosaminoglycanes.

The results of longterm treatment with each of the 8 substances specified above are shown in Example 2 (treatment for 12 weeks) and Example 4 (treatment for 10 weeks).

No significant differences between control and treatment groups was identified with respect to bodyweight and weight of eyes.

EXAMPLE 2

Long Time Treatment of 3 Month with Each of the Four Substances, Caffeine, L-cysteine, Teofylamin, and Fluoxetine and the Effect on the Biochemical Changes in Rabbit Sclera

TABLE 5

Content of collagen specific amino acids in nanomol/mg tissue (dried weight defatted weight) from anterior sclera (Wilcoxon test. *$p < 0.05$), and the increase (Inc.) or decrease (Decr.) compared to the control.

|  | Hydroxyproline | Hydroxylysine | Proline |
| --- | --- | --- | --- |
| Control | 604 +/− 50 | 41 +/− 12 | 886 +/− 29 |
| Fluoxetine | 619 +/− 40 | 33 +/− 11 | 896 +/− 21 |
| Teofylamin | 653 +/− 39 | 28 +/− 10 | 958 +/− 23 |
| Caffeine | 688 +/− 36* | 39 +/− 19 | 993 +/− 18* |
| L-cystine | 599 +/− 41 | 45 +/− 10 | 885 +/− 22 |
|  | Inc. Decr. | Inc. Decr. | Inc. Decr. |
| Fluoxetine | — — | — 20% | — — |
| Teofylamin | 8% — | — 32% | 8% — |
| Caffeine | 14% — | — — | 12% — |
| L-cystine | — — | — — | — — |

TABLE 6

Content of collagen specific amino acids in nanomol/mg tissue (dried weight and defatted weight) from posterior sclera (Wilcoxon test.), and the increase (Inc.) or decrease (Decr.) compared to the control.

|  | Hydroxyproline | Hydroxylysine | Proline |
| --- | --- | --- | --- |
| Control | 547 +/− 141 | 43 +/− 12 | 810 +/− 86 |
| Fluoxetine | 640 +/− 31 | 41 +/− 13 | 927 +/− 15 |
| Teofylamin | 643 +/− 74 | 28 +/− 15 | 902 +/− 53 |
| Caffeine | 668 +/− 61 | 37 +/− 16 | 947 +/− 38 |
| L-cystine | 596 +/− 39 | 43 +/− 8 | 867 +/− 14 |

TABLE 6-continued

Content of collagen specific amino acids in nanomol/mg tissue (dried weight and defatted weight) from posterior sclera (Wilcoxon test.), and the increase (Inc.) or decrease (Decr.) compared to the control.

|  | Hydroxyproline | | Hydroxylysine | | Proline | |
|---|---|---|---|---|---|---|
|  | Inc. | Decr. | Inc. | Decr. | Inc. | Decr. |
| Fluoxetine | 17% | — | — | — | 15% | — |
| Teofylamin | 18% | — | — | 35% | 11% | — |
| Caffeine | 22% | — | — | 14% | 17% | — |
| L-cystine | 9% | — | — | — | 7% | — |

TABLE 7

Content of proteoglycanes in µg PG/mg tissue (wet weight) (Wilcoxon test. *p < 0.05), and the increase or decrease compared to the control.

|  | Anterior sclera | Posterior sclera |
|---|---|---|
| Control | 2.7 +/− 0.2 | 2.7 +/− 0.2 |
| Fluoxetine | 2.2 +/− 0.4* | 2.6 +/− 0.2 |
| Teofylamin | 2.4 +/− 0.5 | 2.7 +/− 0.3 |
| Caffeine | 3.2 +/− 0.8 | 3.2 +/− 0.5 |
| L-cystine | 3.5 +/− 0.5* | 3.5 +/− 0.4* |

|  | Increase | Decrease | Increase | Decrease |
|---|---|---|---|---|
| Fluoxetine | — | 19% | — | — |
| Teofylamin | — | 11% | — | — |
| Caffeine | 19% | — | 19% | — |
| L-cystine | 29% | — | 29% | — |

Conclusion

Fluoxetine: Treatment with fluoxetine (a serotonin re-uptake inhibitor) for three months decreased the content of proteoglycanes in anterior sclera by 19%. Hydroxylysine in the anterior sclera is decreased with 20% and hydroxyproline and proline are increased with 17% and 15%, respectively, in the posterior sclera.

Teofylamin: Treatment with Teofylamin for 3 months reduces the content of proteoglycanes in sclera by 11% (at the front)

Caffeine: Treatment with caffeine for three months increases the content of proteoglycanes in sclera by 19% (to the front) and 19% (to the back). The content of the collagen specific amino acids hydroxyproline and proline are increased by 22% and 17%, respectively, in sclera tests in the back of the eye. Accordingly, the example shows that treatment of a young mammal with caffeine in a moderate dosage results in a strong increase in the content of proteoglycanes as well as in collagen specific amino acids in sclera.

L-cystine: Treatment of young rabbits for three months with L-cystine increases the content of proteoglycanes in the sclera by 29% in both the front and in the back of eye. The content of the collagen specific amino acids hydroxyproline and proline are increased by 9% and 7%, respectively, in sclera samples from the back of the eye. Accordingly, the example shows that treatment with a relative large dosage of L-cystine also increases the content of proteoglycanes, but that the effect on the content of collagen specific amino acids is ambiguous.

EXAMPLE 3

Myopia Progression Stopped by Treatment with Caffeine and L-cystine

A boy presented with myopia at the age of 9 years. Earlier examination showed no ametropia. He had severely progrediating myopia and was treated with a combination of caffeine (100 mg/day) and L-cystine (200 mg/day) for three months followed by a control period of three months with no treatment, and subsequently a new treatment period followed by a control period, etc. In total 4 treatment periods and 4 control periods alternated.

Measurement of the axial length of the eye was made by means of Auto Axial Biometer AL-010, Shin-Nippon.

Table 8 and Table 9 shows the average growth in the axial length of both eyes in the 4 treatment periods and the 4 control periods, respectively.

TABLE 8

Treatment with caffeine 50 mg × 2 and L-cystine 100 mg × 2 (tablets) from day 0–90, day 161–289, and 412–570.
Axial length in mm RE = right eye, LE = left eye.

| Day | RE | LE |
|---|---|---|
| 0 | 23.74 | 23.70 |
| 57 | 23.86 | 23.58 |
| 118 | 24.06 | 23.83 |
| 161 | 24.14 | 24.07 |
| 227 | 24.21 | 24.03 |
| 260 | 24.26 | 24.10 |
| 289 | 24.24 | 24.22 |
| 350 | 24.43 | 24.44 |
| 392 | 24.56 | 24.47 |
| 412 | 24.59 | 24.39 |
| 447 | 24.63 | 24.53 |
| 476 | 24.73 | 24.52 |
| 503 | 24.74 | 24.53 |
| 541 | 24.72 | 24.49 |
| 570 | 24.71 | 24.55 |

TABLE 9

Average growth during treatment and control periods, respectively.

|  | Axial length growth | n |
|---|---|---|
| Caffeine + L-cysteine (100 + 200 mg/day) | 0.089 mm | 4 |
| Control period | 0.253 mm | 4 |

Conclusion: Example 3 confirms that treatment with a combination of caffeine and L-cystine actually is able to inhibit the myopia progression in a child as a significant effect of the treatment with a factor of 3 (inhibition of growth) in relation to no treatment is demonstrated in study.

EXAMPLE 4

The Effect of the Caffeine Metabolite 7-Methylxanthine (Heteroxanthine) 50 mg per Animal Daily on Scleras Content of Proteoglycanes and Collagen Specific Amino Acids The effect of the caffeine metabolite 3,7-dimethylxanthine (theobromine) 50 mg per animal daily on scleras content of proteoglycanes and collagen specific amino acids.

The effect of acetazolamide 50 mg per animal daily on scleras content of proteoglycanes and collagen specific amino acids.

The effect of 500 mg per animal daily of L-ornithine on scleras content of proteoglycanes and collagen specific amino acids.

Conclusion: No significant differences were found as regards the content of proteoglycans in the sclera samples, but there was a near significant increase in 7-methylxanthine treated posterior sclera, and a decrease in theobromine treated posterior sclera.

Significant higher content of all collagen specific amino acids, except hydroxylysine in anterior sclera, was found in all sclera samples from theobromine (3,7-dimethylxanthine) treated animals. Animals treated with 7-methylxanthine showed significantly higher content of hydroxyproline and proline in posterior sclera. Treatment with acetazolamide reduced the content of hydroxyproline and proline in anterior sclera significantly.

TABLE 10

Content of proteoglycanes in μg PG/mg tissue (wet weight)

|  | anterior sclera |  | posterior sclera |  |
| --- | --- | --- | --- | --- |
| Control | 2.9 +/− 0.5 |  | 2.9 +/− 0.4 |  |
| 7-methylxanthine | 2.5 +/− 0.5 |  | 3.3 +/− 0.3 |  |
| 3,7-dimethylxanthine | 2.6 +/− 0.7 |  | 2.5 +/− 0.4 |  |
| Acetazolamide | 2.9 +/− 0.4 |  | 2.8 +/− 0.8 |  |
| L-ornithine | 3.0 +/− 1.1 |  | 3.0 +/− 0.9 |  |
|  | Increase | Decrease | Increase | Decrease |
| 7-methylxanthine | — | 14% | 14% | — |
| 3,7-dimethylxanthine | — | 10% | — | 14% |
| Acetazolamide | — | — | — | — |
| L-ornithine | — | — | — | — |

TABLE 11

Content of collagen specific amino acids in nanomol/mg tissue (dried weight defatted weight) from anterior sclera. (Wilcoxon test. *p < 0.05)

|  | Hydroxyproline | Hydroxylysine | Proline |
| --- | --- | --- | --- |
| Control | 638 +/− 24 | 45 +/− 10 | 928 +/− 56 |
| 7-methylxanthine | 667 +/− 73 | 45 +/− 3 | 951 +/− 111 |
| 3,7-dimethylxanthine | 751 +/− 53* | 49 +/− 6 | 1073 +/− 78* |
| Acetazolamide | 596 +/− 27* | 41 +/− 4 | 843 +/− 47* |
| L-ornithine | 605 +/− 37 | 37 +/− 4 | 875 +/− 48 |

TABLE 12

Content of collagen specific amino acids in nanomol/mg tissue dried weight and defatted weight) from posterior sclera. (Wilcoxon test. *p < 0.05)

|  | Hydroxyproline |  | Hydroxylysine |  | Proline |  |
| --- | --- | --- | --- | --- | --- | --- |
|  | \multicolumn{2}{}{} |  |  |  |  |  |
| Control | 622 +/− 59 |  | 41 +/− 5 |  | 864 +/− 67 |  |
| 7-methylxanthine | 719 +/− 81* |  | 44 +/− 7 |  | 1018 +/− 108* |  |
| 3,7-dimethyl-xanth. | 741 +/− 18* |  | 49 +/− 4* |  | 1029 +/− 45* |  |
| Acetazolamide | 563 +/− 91 |  | 38 +/− 6 |  | 781 +/− 125 |  |
| L-ornithine | 611 +/− 24 |  | 38 +/− 5 |  | 871 +/− 35 |  |
|  | Inc. | Decr. | Inc. | Decr. | Inc. | Decr. |
| 7-methylxanthine | 16% | — | 7% | — | 10% | — |
| 3,7-dimethyl-xanth. | 19% | — | 20% | — | 20% | — |
| Acetazolamide | — | 10% | — | 7% | — | 10% |
| L-ornithine | — | — | — | 7% | — | — |

EXAMPLE 5

Effect on Proteoglyeanes Compared with Effect on [$^3$H Ryanodine Binding of Different Xanthines Comparison of effect on proteoglycanes content of posterior sclera in % to control with effect on [$^3$H ryanodine binding in % compared to control.

TABLE 13

|  | Effect on proteoglycan content of posterior sclera in % compared to control | Effect on [$^3$H ryanodine binding in % compared to control |
| --- | --- | --- |
| Caffeine | 119 | 240 |
| Theophylline | 100 | 136 |
| 7-methylxanthine | 114 | 204 |
| Theobromine | 86 | 124 |

(Theobromine = 3,7-dimethylxanthine)

EXAMPLE 6

Extraction Method

The plant material must either be extracted immediately after, harvesting or stored at −20° C. until extraction take place, and preferable, the material is freeze-dried before the cold storage. The material is finely ground and boiled for 20 minutes with 0.0125 N sulphuric acid. After cooling the extract is applied to a column packed with siliceous earth (Extralut, Merck), 700 p per liter of extract, and after 10 minutes the column is eluted with a 4-fold volume of chloroform. The chloroform phase is eluted to dryness and chloroform condensed and collected for re-use. The residue contains the methylxanthines.

EXAMPLE 7

The plant material must either be extracted immediately after harvesting or stored at −20° C. until extraction can take place, and preferable, the material must be freeze-dried before the cold storage. The material is finely ground and boiled for 20 minutes with =0.1 N hydrochloric acid. After cooling the extract is filtered and applied to a column packed with polyvinylpyrrolidone powder, and after 10 minutes the column is eluted with water. The fraction of the eluate which has a high concentration of the methylxanthine in question is collected and evaporated to a standardized concentration of this substance.

EXAMPLE 8

Experiments Under Investigation

A) The effect of the caffeine metabolite 3,7-dimethylxanthine (theobromine) on c-wave by ERG and the standing potential of the eye is under investigation.

B) The effect of the caffeine metabolite 7-methylxanthine (heteroxanthine) on c-wave by ERG and the standing potential of the eye is under investigation.

C) Pilot projects

Substances to be tested for treatment or preventing of myopia:

1) Caffeine and L-cystine (dosages as described)
2) 7-methylxanthine 250 mg
3) Pentifylline 250 mg Substances to be tested for treatment or preventing of hypermetropia:

4) 1,9-dimethylxanthine 250 mg
5) theobromine 250 mg (may be used once or twice daily equivalent of 10 or 20 mg per kg per day with a body weight of 25 kg)

The Test Conditions:

Caffeine and L-cystine are to be given as tablets for the inhibition of the progression of myopia in a group of children aged 10–14.

The Background of the Test

The content of L-cystine in the food varies depending on whether the protein need is covered by e.g. fish (approximately 350 mg L-cystine per day for a child weighing 30 kg) or wheat bread (approximately 700 mg L-cystine per day) (Garrow, J. S.: Human Nutrition and Dietetics, Churchill Livingstone, 1993). L-cystine is absorbed through the intestine, the part that is not used for the building up of the proteins of the body is burnt on equal terms with e.g. sugar.

Caffeine is a well-known component of e.g. coffee, tea, chocolate and cola soft drinks. One cup of coffee contains 100–150 mg of caffeine, one cup of tea approximately 60 mg, one cup of cocoa approximately 5 mg, and one glass of cola approximately 20 mg. Only a very small part of the caffeine in cola comes from the cola nut, primarily it is a matter of added caffeine. Thus it has been calculated that the total consumption of caffeine in cola in the U.S.A. corresponds to the amount deriving by way of decaffeinating coffee in the country (James, J. E.: Caffeine and Health, Academic Press, 1991).

From the above foods children in the U.S.A. aged 10–17 consume approximately 1.5 mg of caffeine per kg weight per day, i.e. for a child of 30 kg approximately 45 mg per day (Albeit, M. L.: Journal of the American Dietetic Association, 88, 466–471 (1988). A Finnish examination showed that approximately 40% of children aged 12 consumed one or more cups of coffee per day. An even larger percentage consumed tea or hot chocolate every day (55<, E.: Social Science and Medicine, 26, 259–264 (1988).

L-cystine is an important factor in the stabilisation of the collagen molecules in the sclera as it forms the basis of sulphurous cross-links. Therefore, it is possible that, in a period with heavy body weight increase, a relative lack of L-cystine can lead to an unstable collagen and thus participate in developing myopia.

Therefore it is possible that supplementing the diet with L-cystine can inhibit the development of myopia.

Candidates of substances applicable for treatment of such a relatively benign condition as myopia in so many children must necessarily be free of almost any side effects.

Caffeine and L-cystine comply with this condition. Treating a 9-year old boy with severely increasing myopia (Example 3) also implies an effect as the axial longitudinal growth over a period of three months was reduced from 0.253 mm to 0.089 mm with caffeine 100 mg+L-cystine 200 mg per day. The treatment showed no side effects.

The normal longitudinal growth of the human eye for the age of 3–14 amounts to approximately 0.1 mm per year, but there is much variation. In approximately 15% the axial longitudinal growth is thus >0.4 mm per year (Sorsby, A., Med. Res. Counc. spec. Rep. Ser., No.301, London, 1962). Particularly this group develops myopia.

C. Test Persons

Boys and Girls aged 10–14 with Progreding Myopia

Inclusion: 3×12 myopic persons, 10×14 years old, glass strength>−1.25.

Exclusion: Severe ordinary disease (e.g. asthma, epilepsy, diabetes, physical disease), severe congenital myopia, other severe eye diseases (e.g. congenital cataract, ceratoconus, chronic iritis, glaucoma).

The test persons were recruited from practising ophthalmologists.

As myopia develops in the childhood it is necessary to apply children in the test.

e. Method

Pilot Test 12 persons are treated with tablets of caffeine, 50 mg in the morning and 50 mg in the evening for 6 months.

12 persons are treated with tablets of L-cystine, 100 mg in the morning and 100 mg in the evening for 6 months.

12 persons are treated with tablets of caffeine, 50 mg, and tablets of cystine, 100 mg in the morning and in the evening for 6 months.

Then a control period of 6 months follows with no treatment. The level of myopia progression for the two periods is compared for each participant.

Furthermore, the myopia progression in the treatment period is compared with existing material concerning myopia progression in children of the same age group (e.g. Jensen, H.: Myopia progression in young school children, Acta Ophthal., Suppl. 200, Vol 69, 1991).

During the test the following examinations are made:
1. Status at the commencement of the test.
   a. Subjective measuring of glass strength (ordinary glass determination)
   b. Refraction determination with auto refractor (objective determination of the glass strength) in cyclogylcycloplegy (cancelling the accommodation reflex with cyclogyl drops).
   c. Measuring the axial length with Shin-Nippon axial length measurer. The patient is dripped with local anaesteticum, and an ultra sound probe is put on the eye by means of a tonometer set at 15 mmHg. The axial length is stated in mm by the apparatus by 2 digits.
      Three measurements are made and the average is calculated.
2. Measurement of the axial length after two months (as 1c).
3. Measurement of the axial length after 4 months (as 1c).
4. Status after 6 months (as 1a–c).
5. Measurement of the axial length after 8 months (as 1c).
6. Measurement of the axial length after 10 months (as 1c).
7. Status after 12 months (as 1a–c).

Data identifying the patient is destroyed at the end of the test.

TABLE A

STANDARD RABBIT DIET (STANRAB)

| Crude Oil | % | 3.1 | Glycine | % | 1.39 |
|---|---|---|---|---|---|
| Crude Protein | % | 16.7 | Aspartic acid | % | 1.14 |
| Crude Fibre | % | 14.8 | Glutamic acid | % | 3.01 |
| Ash | % | 8.1 | Proline | % | 1.18 |
| N.F.E. | % | 47.3 | Serine | % | 0.70 |
| Dig, Crude Oil | % | 2.8 | Hydroxyproline | % | — |
| Dig, Crude Protein | % | 14.9 | Hydroxylysine | % | — |
| Tot, Dietary Fibre | % | 31.9 | Alanine | % | 0.11 |
| Pectin | % | 2.4 | Calcium | % | 0.83 |
| Hemicellulose | % | 14.7 | Total Phosphorous | % | 0.61 |
| Cellulose | % | 11.7 | Phytate Phosphorous | % | 0.36 |

TABLE A-continued

STANDARD RABBIT DIET (STANRAB)

| | | | | | |
|---|---|---|---|---|---|
| Lignin | % | 3.1 | Available Phosphorous | % | 0.25 |
| Starches | % | 22.7 | Sodium | % | 0.25 |
| Sugars | % | 7.5 | Chlorine | % | 0.36 |
| Gross Energy | mj/kg | 14.8 | Magnesium | % | 0.41 |
| Dig, Energy | mj/kg | 9.1 | Potassium | % | 1.52 |
| Met, Energy | mj/kg | 8.2 | Iron | mg/kg | 194.0 |
| Myrletoleic acid | % | 0.02 | Copper | mg/kg | 17.0 |
| Palmitoileic acid | % | 0.09 | Manganese | mg/kg | 93.0 |
| Oleic acid | % | 0.79 | Zinc | mg/kg | 47.0 |
| Linoleic acid | % | 0.75 | Cobalt | mcg/kg | 535.0 |
| Linolenic acid | % | 0.18 | Iodine | mcg/kg | 665.0 |
| Arachidonic acid | % | 0.15 | Selenium | mcg/kg | 217.0 |
| Clupanodonic acid | % | — | Fluorine | mg/kg | 24.0 |
| Lauric acid | % | 0.03 | Retinol | mcg/kg | 47473.0 |
| Myristic acid | % | 0.18 | Vitamin A | iu/kg | 156991.0 |
| Palmitic acid | % | 0.37 | Cholecalciferol | mcg/kg | 37.6 |
| Stearic acid | % | 0.07 | Vitamin D3 | iu/kg | 1504.0 |
| Arginine | % | 1.21 | α-Tocopherol | mg/kg | 62.0 |
| Lysine | % | 0.91 | Vitamin E | mg/kg | 68.2 |
| Methionine | % | 0.35 | Vitamin B1 | mg/kg | 10.6 |
| Cystine | % | 0.29 | Vitamin B2 | mg/kg | 14.2 |
| Tryptophan | % | 0.28 | Vitamin B6 | mg/kg | 7.6 |
| Histidine | % | 0.44 | Vitamin B12 | mcg/kg | 11.0 |
| Threonine | % | 0.68 | Vitamin C | mg/kg | 113.0 |
| Isoleucine | % | 0.74 | Vitamin K3 | mg/kg | 63.2 |
| Leucine | % | 1.28 | Folic acid | mg/kg | 2.1 |
| Phenylalanine | % | 0.82 | Nicotinic acid | mg/kg | 73.8 |
| Valine | % | 0.88 | Pantothenic acid | mg/kg | 34.7 |
| Tyrosine | % | 0.62 | Choline | mg/kg | 1151.0 |
| Taurine | % | — | Inositol | mg/kg | 1515.0 |
| | | | Biotin | mcg/kg | 344.0 |
| | | | p-aminobenzoic acid | mg/kg | — |
| | | | β-Carotene | mg/kg | 99.2 |
| | | | Xanthophyl | mg/kg | — |

1. All values calculated to a nominal 10% moisture content.
2. Values are total calculated values.
3. 1 mcg Retinol nid 3.3 i.u. vitamin A.
4. Total Retinol content includes the Retinol equivalent of β-Carotene.
5. 1 mcg Cholecalciferol = 40 i.u. vitamin D3 activity.
6. 1 mcg β-Carotene = 1.6 i.u. vitamin A activity.
7. 1 mg α-Tocopherol = 1.1 i.u. vitamin E activity.
8. 1 MJ = 239.23 Calories

What is claimed is:

1. A method of treating an eye disorder characterized by an abnormal past rate of longitudinal growth of the eye by altering the subsequent rate of longitudinal growth of the eye so as to at least partially counteract said abnormal past rate, comprising administering to an individual in need thereof a therapeutically effective amount of one or more substances selected from the group of compounds of the general formula I, II and III

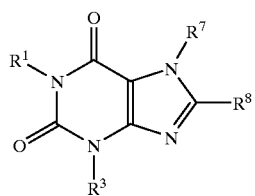

(I)

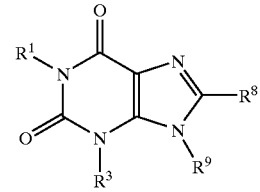

(II)

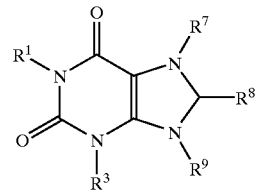

(III)

wherein $R^1$, $R^3$, $R^7$, and $R^9$ are independently selected from the group consisting of hydrogen, optionally substituted $C_{1-20}$-alkyl, optionally substituted $C_{2-20}$-alkenyl, optionally substituted $C_{4-20}$-alkadienyl, optionally substituted $C_{6-20}$-alkatrienyl, optionally substituted $C_{2-20}$-alkynyl, optionally substituted $C_{1-20}$-alkoxycarbonyl, optionally substituted $C_{1-20}$-alkylcarbonyl, formyl, optionally substituted aryl, optionally substituted aryloxycarbonyl, optionally substituted arylcarbonyl, optionally substituted heteroaryl, optionally substituted heteroaryloxycarbonyl, optionally substituted heteroarylcarbonyl, carbamoyl, mono- and di($C_{1-20}$-alkyl)aminocarbonyl, mono- and di($C_{1-20}$-alkyl)amino-$C_{1-20}$-alkyl-aminocarbonyl, and halogen, and $R^8$ is selected from the group consisting of hydrogen, optionally substituted $C_{1-20}$-alkyl, optionally substituted $C_{2-20}$-alkenyl, optionally substituted $C_{4-20}$-alkadienyl, optionally substituted $C_{6-20}$-alkatrienyl, optionally substituted $C_{2-20}$-alkynyl, optionally substituted $C_{1-20}$-alkoxy, optionally substituted $C_{2-20}$-alkenyloxy, carboxy, hydroxy, optionally substituted $C_{1-20}$-alkoxycarbonyl, optionally substituted $C_{1-20}$-alkylcarbonyl, formyl, optionally substituted aryl, optionally substituted aryloxycarbonyl, optionally substituted aryloxy, optionally substituted arylcarbonyl, optionally substituted arylcarbonyl, optionally substituted heteroaryl, optionally substituted heteroaryloxycarbonyl, optionally substituted heteroaryloxy, optionally substituted heteroarylcarbonyl, amino, mono- and di($C_{1-20}$-alkyl) amino, carbamoyl, mono- and di($C_{1-20}$-alkyl) aminocarbonyl, amino-$C_{1-20}$-alkyl-aminocarbonyl, mono- and di($C_{1-20}$-alkyl) amino-$C_{1-20}$-alkyl-aminocarbonyl, optionally substituted $C_{1-20}$-alkylcarbonylamino, guanidino, carbamido, optionally substituted $C_{1-20}$-alkanoyloxy, sulphono, optionally substituted $C_{1-20}$-alkylsulphonyloxy, nitro, sulphanyl, optionally substituted $C_{1-20}$-alkylthio, and halogen, in which at least one of the substances is administered systemically.

2. Method according to claim 1, wherein $R^1$, $R^3$, $R^7$, and $R^9$ are independently selected from the group consisting of hydrogen, optionally substituted $C_{1-6}$-alkyl, optionally substituted $C_{2-6}$-alkenyl, optionally substituted $C_{2-6}$-alkynyl, optionally substituted $C_{1-6}$-alkylcarbonyl, formyl, optionally substituted aryl, optionally substituted arylcarbonyl, optionally substituted heteroaryl, and optionally substituted heteroarylcarbonyl, and $R^8$ is selected from the group consisting of hydrogen, optionally substituted $C_{1-6}$-alkyl, optionally substituted $C_{2-6}$-alkenyl, optionally substituted $C_{2-6}$-alkynyl, optionally substituted $C_{1-6}$-alkoxy, optionally substituted $C_{2-6}$-alkenyloxy, carboxy, hydroxy, optionally substituted $C_{1-6}$-alkoxycarbonyl, optionally substituted $C_{1-6}$-alkylcarbonyl, formyl, optionally substituted aryl, optionally substituted aryloxycarbonyl, optionally substituted aryloxy, optionally substituted arylcarbonyl, optionally substituted arylcarbonyl, optionally substituted heteroaryl, optionally substituted heteroaryloxycarbonyl, optionally substituted heteroaryloxy, optionally substituted heteroarylcarbonyl, amino, mono- and di($C_{1-6}$-alkyl) amino, carbamoyl, mono- and di($C_{1-6}$-alkyl) aminocarbonyl, optionally substituted $C_{1-6}$-alkylcarbonylamino, guanidino, carbamido, optionally substituted $C_{1-6}$-alkanoyloxy, sulphono, optionally substituted $C_{1-6}$-alkylsulphonyloxy, nitro, sulphanyl, optionally substituted $C_{1-6}$-alkylthio, and halogen.

3. A method according to claim 1 wherein the substance is administered systematically.

4. A method according to claim 1 wherein the substance is administered topically.

5. The method according to claim 1 wherein the treatment is by use of a preparation in the form suitable for topical application on skin.

6. The method according to claim 1 wherein the treatment is with a preparation in a form suitable for implantation, injection or systemic administration.

7. A method according to claim 1 wherein the substance or the mixture of said substances is administered in a medicament comprising the substances in an amount of 1–10% by weight of the medicament.

8. A method according to claim 1 wherein the substance is administered in a dosage of 7.5–750 mg and is administered 1–4 times daily.

9. The method according to claim 1 comprising administration 1–4 times daily of the substance when the treatment is not by implantation.

10. A method according to claim 1 wherein the substance or a mixture of substances are extracted from natural sources.

11. The method of claim 1 in which the substance is a prostaglandin agonist.

12. The method of claim 1 in which the eye disorder is myopia, and the treatment reduces the subsequent rate or period of longitudinal growth.

13. The method of claim 12 wherein said individual exhibits a c-wave having an amplitude and/or a standing potential which can be measured by electro retinography wherein the substance increases, upon administration or application of the substance, the standing potential and/or the amplitude of the c-wave measured by electro retinography (ERG) and/or increases ryanodine receptor (RyR) and/or inositol trisphosphate ($IP_3$) receptor binding.

14. The method of claim 12 in which the subsequent growth rate is less than average longitudinal growth rate in normal individuals of the same age.

15. The method of claim 12 in which the substance shows an effect on [$^3$H] ryanodine binding of more than 200% relative to unsubstituted xanthine.

16. The method of claim 1 in which the eye disorder is hypermetropia and the treatment increases the subsequent rate or period of longitudinal growth.

17. The method of claim 16 wherein the substance decreases, upon administration or application of the substance, standing potential and/or amplitude of the c-ave measured by electro retinography (ERG) and/or decreases ryanodine receptor (RyR) and/or inositol trisphosphate ($IP_3$) receptor binding.

18. The method of claim 16 in which the subsequent growth rate is more than average longitudinal growth rate in normal individuals of the same age.

19. The method of claim 16 in which the substance shows an effect on [$^3$H] ryanodine binding of less than 110% relative to unsubstituted xanthine.

20. The method of claim 17 wherein the decrease correspond to at least 10% compared to the initial value.

21. The method of claim 13 wherein the increase corresponds to at least 10% compared to the initial value.

22. The method of claim 1 in which the individual is a human.

23. The method of claim 22 in which the individual is non-glaucomic.

24. The method of claim 1 in which the individual is a human whose age at the time treatment commences is under 20 years of age.

25. The method of claim 1 in which the individual is a human whose age at the time treatment commences is under 12 years of age.

26. Method of claim 12 comprising administering to said individual in need thereof a therapeutically effective amount of one or more substances selected from caffeine;

1,7-dimethylxanthine (paraxanthine), 3,7-dimethylxanthine (theobromine);

7-methylxanthine (heteroxanthine), 3-methylxanthine; 1-methylxanthine, isobutylmethylxanthine (IBMX);

1-Hexyl-3,7-dimethylxanthine (pentifylline);

1,7-Dimethyl-xanthine;

1,3-Dipropyl-7-methyl-xanthine;

7-Propyixanthine;

7b-Chloroethyl-1,3-dimethylxanthine;

3,7-Dimethyl-1-propargyl-xanthine;

3-Propylxanthine;

1-(5-Oxohexyl)-3,7-dimethylxanthine (pentoxyfylline);

3-Isobutyl-1-methylxanthine;

3,9-Dimethyixanthine;

8-Cyclopentyl-1,3-dimethylxanthine;

1,3-Bis(3-methylbut-2-butenyl-7-methylxanthine;

3,7-Dihydro-7-methyl-1,3-dipropyl-1H-purine-2,6-dione;

7-Methyl-1,3-diprenylxanthine(7-methyl-1,3-dipropyl-xanthine; 7-Ethoxymethyl-1-(5-hydroxy-5-methylhex-methylxanthine (Torbafylline);

1-(5 hydoxy-5-methylhexyl)-3-methyl-7-propylxanthine;

3,7-Dimethyl-1-(5-oxyhexyl)-xanthine (Pentoxifylline, "Trental");

3,7-Dimethyl-1-(5-hydroxyhexyl)-xanthine (Hydroxypentoxifylline);

1-Hexyl-3,7-dimethylxanthine (Pentifylline, "Cosaldon");

3,7-Dimethyl-1-proparglyxanthine (DMPX);

(E)-8-(3,4-Dimethoxystyryl)-1,3-dipropyl-7-methylxanthine (KF 17837) (Lisofylline);

1-(5-Hydroxy-5-methylhexyl)-3-methylxanthine (Albifylline);

3-Methyl-1-(5'-oxohexyl)-7-propylxanthine (Propentofylline);

1-(5-Hydroxyhexyl)-3,7-dimethylxanthine;

(E)-1,3-dipropyl-8-(3,4-dimethoxystyryl)-7-methylxanthine;

1,3-di-n-butyl-7-(2'oxopropyl)-xanthine (Denbufylline);
1-n-butyl-3-n-propylxanthine;
7-(2,3-dihydroxypropyl)-theophylline (Dyphylline);
7-Methyl-8-(2-hydroxy-N-methylethylamino)-theophylline (Cafaminol);
7-(1,3-Dioxolan 2-ylmethyl)-theophylline (Doxofylline);
7-(2-Hydroxyethyl)-1,3-dimethylxanthine (Etofylline);
7-(2-Hydroxypropyl)-1,3-dimethylxanthine (Proxyphylline);
Pyridoxine-O-(theophyllin-7-ylethyl)sulphate (Pyridofylline);
7-(2-(3-diethylcarbamoylpropionyloxy)ethyl) theophylline (Suxamidofylline);
Piperazine bis(theophyllin-7-ylacetate)(Acepifylline);
8-benzyl-7-(2-(N-ethyl-N-2-hydroxyethylamino)ethyl) theo-phylline (Bamifylline);
2-amino-2-methylpropan-1-ol theophyllinate (Bufylline);
7-(2,3-Dihydroxypropyl)-1,3-dimethylxanthine (Diprophylline);
7-(2-diethylamoinoethyl)-1,3-dimethylxanthine camphor sulphonate (Etamiphylline Camsylate);
3-Propylxanthine (Enprofylline); and mixtures thereof.

27. The method for treating myopia according to claim 26 comprising administering a mixture of two or more said substances, said mixture having a synergistic effect on the myopia.

28. The method for treating myopia according to claim 26 where at least one said substances is a xanthine and is administered in a dosage of 7.5–750 mg 1–4 times daily.

* * * * *